(12) United States Patent
Kassis

(10) Patent No.: US 9,764,079 B2
(45) Date of Patent: Sep. 19, 2017

(54) METHODS AND APPARATUS FOR ISOLATION OF WHITE BLOOD CELLS USING A MULTIPOSITION VALVE

(71) Applicant: PRESIDENT AND FELLOWS OF HARVARD COLLEGE, Cambridge, MA (US)

(72) Inventor: Amin I. Kassis, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 132 days.

(21) Appl. No.: 14/391,914

(22) PCT Filed: Apr. 12, 2013

(86) PCT No.: PCT/US2013/036353
§ 371 (c)(1),
(2) Date: Oct. 10, 2014

(87) PCT Pub. No.: WO2013/155401
PCT Pub. Date: Oct. 17, 2013

(65) Prior Publication Data
US 2015/0080204 A1    Mar. 19, 2015

Related U.S. Application Data

(60) Provisional application No. 61/623,251, filed on Apr. 12, 2012.

(51) Int. Cl.
*B04B 5/04* (2006.01)
*A61M 1/36* (2006.01)
(Continued)

(52) U.S. Cl.
CPC ......... *A61M 1/3693* (2013.01); *B01L 3/5021* (2013.01); *B04B 5/0414* (2013.01);
(Continued)

(58) Field of Classification Search
CPC ....... B04B 5/04; B04B 5/0404; B04B 5/0421; B04B 5/0442; B04B 5/0414;
(Continued)

(56) References Cited

U.S. PATENT DOCUMENTS 9,573,130 B2 * 2/2017 Hassouneh ............. B01L 3/508
9,610,590 B2 * 4/2017 Hamandi .............. B04B 5/0407
(Continued)

FOREIGN PATENT DOCUMENTS

EP    0119692 A2    9/1984
EP    0312595 A1    4/1989
(Continued)

*Primary Examiner* — Charles Cooley
(74) *Attorney, Agent, or Firm* — Nixon Peabody LLP; David S. Resnick; David F. Crosby

(57) ABSTRACT

Kits and methods provide for the isolation of white blood cells from bodily fluids. In one exemplary aspect, a method for isolating white blood cells from blood includes the act of adding a blood sample to a separation tube having a distal end, a proximal end, and a valve located proximate said proximal end, said valve being configured to transition between at least first, second, and third positions. The method also includes the act of removably attaching a cap to the distal end, centrifuging the separation tube with the valve in the first position, removing the cap at the distal end of the separation tube and removably attaching a first syringe to the proximal end, switching the valve to the second position and withdrawing, via the first syringe, a red blood cell sediment. The method also includes the act of switching the valve to the first position and removing the first syringe, adding a small volume of buffer to the separation tube, removably attaching a cap to the distal end and centrifuging the separation tube and removing the cap at the distal end of the separation tube and removably attaching a second syringe to the proximal end. Additional acts include switching the valve to the second position, withdrawing the remaining red
(Continued)

blood cell sediment via the second syringe and switching the valve to the first position and removing the second syringe.

14 Claims, 16 Drawing Sheets

(51) Int. Cl.
*B01L 3/00* (2006.01)
*A61J 1/20* (2006.01)
(52) U.S. Cl.
CPC ............ *A61J 1/2037* (2015.05); *A61J 1/2051* (2015.05); *A61J 1/2096* (2013.01); *B01L 2200/026* (2013.01); *B01L 2300/0654* (2013.01); *B01L 2300/0851* (2013.01); *B01L 2400/0644* (2013.01)
(58) Field of Classification Search
CPC ............ B01L 3/5021; B01L 2200/026; B01L 2300/0654; B01L 2300/0851; B01L 2400/0644; A61M 1/3693; A61J 1/2037; A61J 1/2096; A61J 1/2051
USPC ......... 494/37, 10, 16, 20; 422/548, 549, 550
See application file for complete search history.

(56) References Cited

U.S. PATENT DOCUMENTS

| | | |
|---|---|---|
| 2002/0182664 A1 | 12/2002 | Doleck et al. |
| 2002/0185457 A1* | 12/2002 | Smith .................... B01L 3/5021 210/787 |
| 2004/0256331 A1* | 12/2004 | Arking ............... B01D 17/0214 210/787 |
| 2006/0273050 A1 | 12/2006 | Higgins et al. |
| 2008/0025877 A1 | 1/2008 | Alley |
| 2011/0111476 A1 | 5/2011 | Faustman et al. |
| 2011/0230328 A1* | 9/2011 | Kinoshita ............. B01L 3/5021 494/28 |
| 2012/0077217 A1 | 3/2012 | Haubert et al. |
| 2017/0028137 A1* | 2/2017 | Mirabito ............... A61M 1/029 |

FOREIGN PATENT DOCUMENTS

| | | | |
|---|---|---|---|
| WO | 98/46362 A1 | 10/1998 | |
| WO | 03050536 A2 | 6/2003 | |
| WO | WO 2010035709 A1 * | 4/2010 | ........... B01L 3/5021 |
| WO | 2010/065018 A1 | 6/2010 | |

* cited by examiner

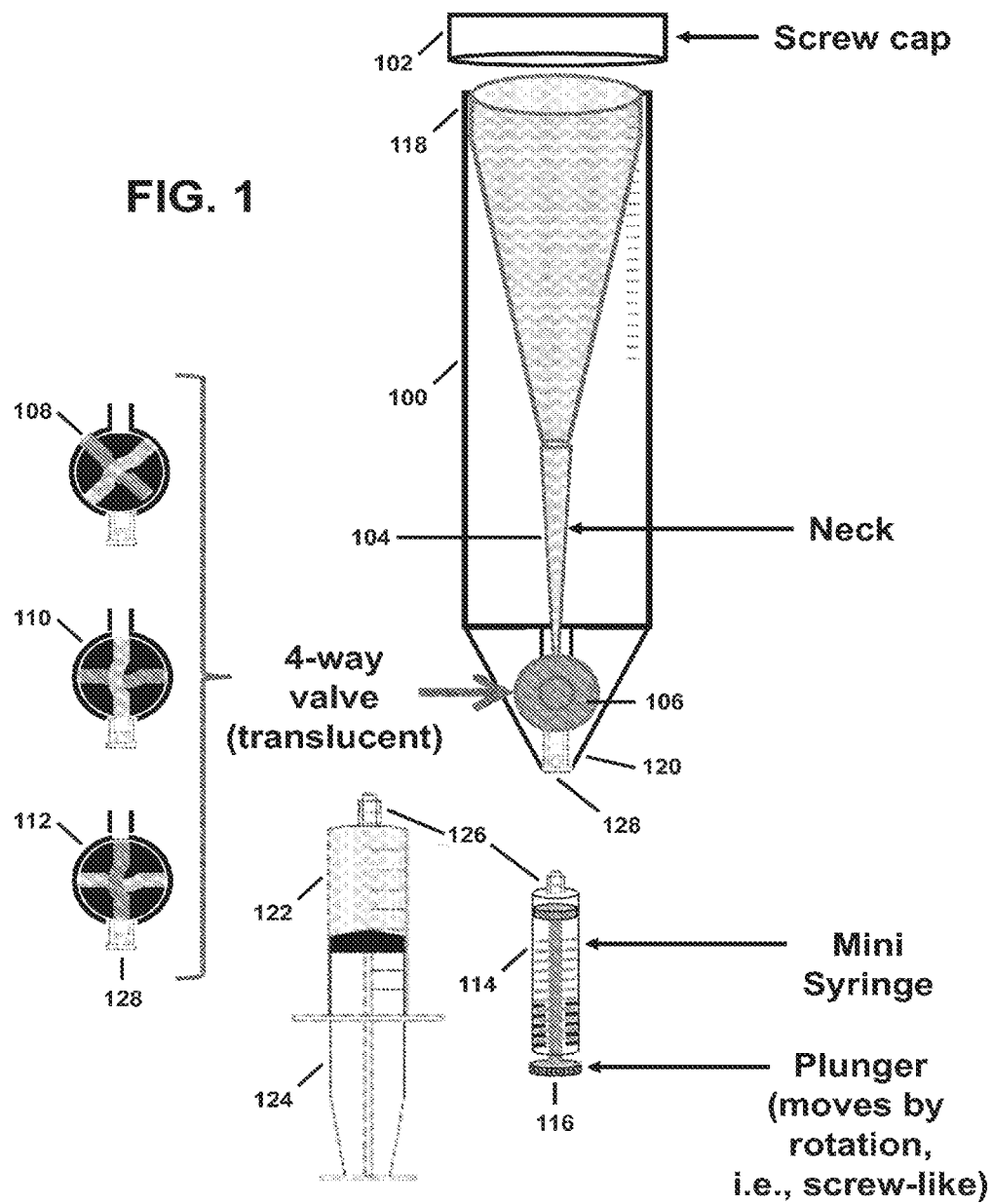

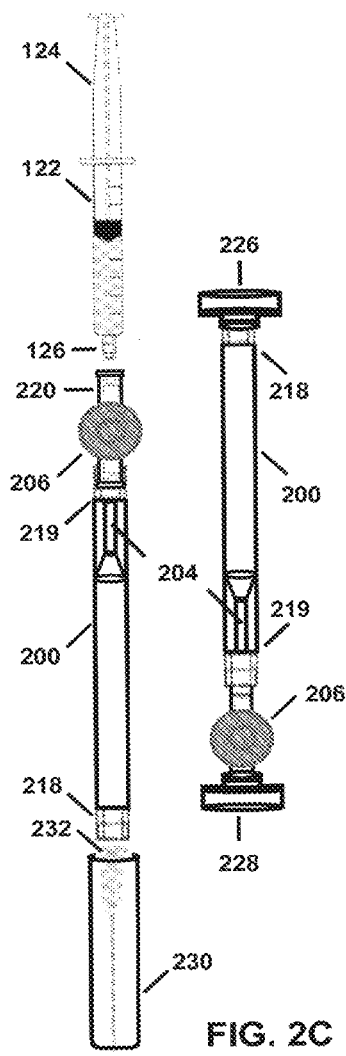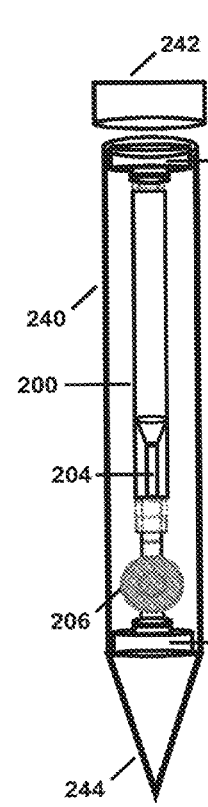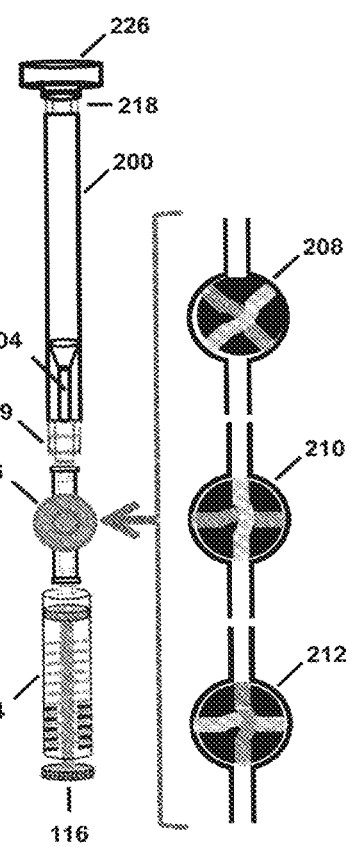
FIG. 2B   FIG. 2C   FIG. 2D   FIG. 2E   FIG. 2F

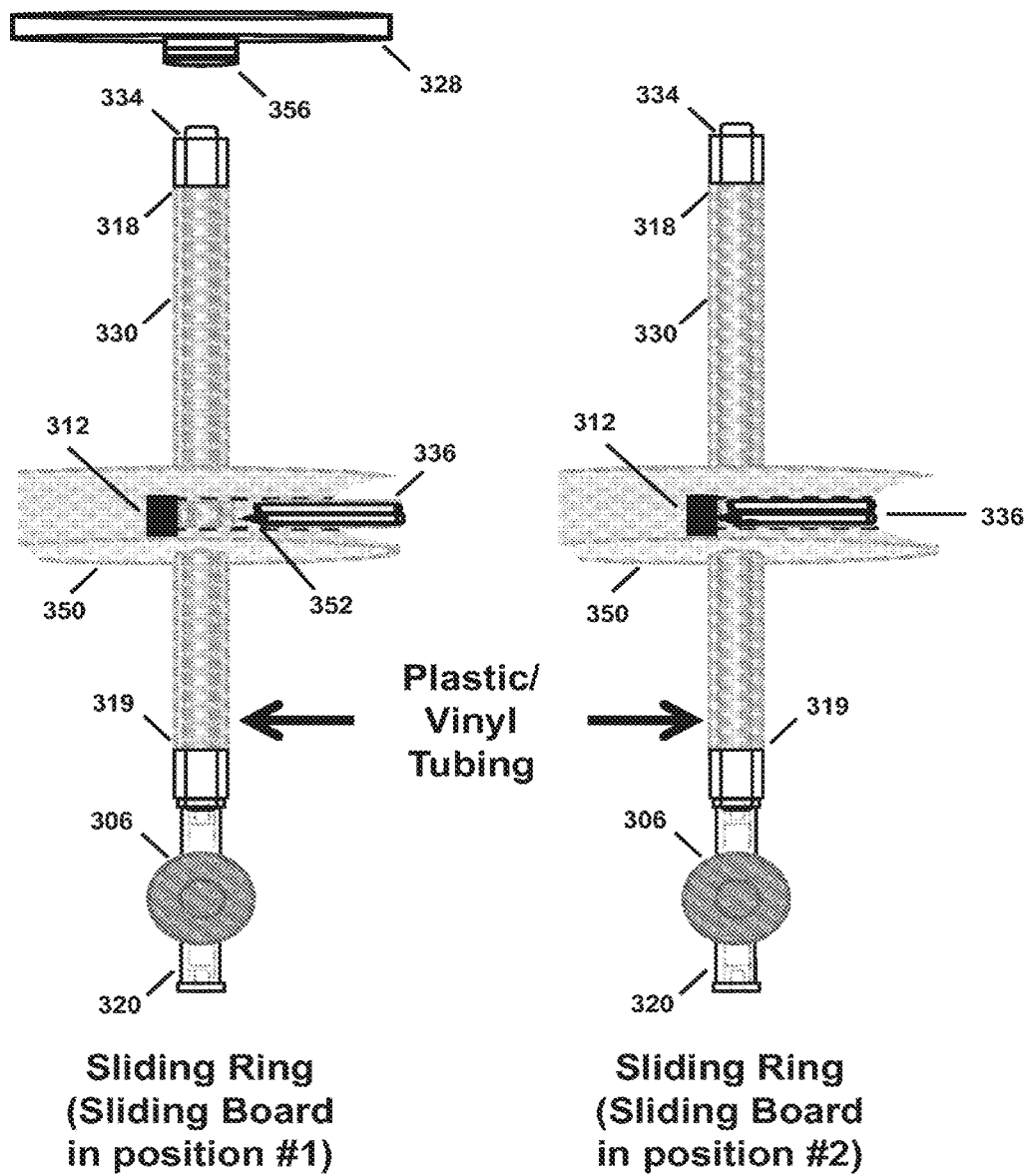
FIG. 3E — Sliding Ring (Sliding Board in position #1)
FIG. 3F — Sliding Ring (Sliding Board in position #2)

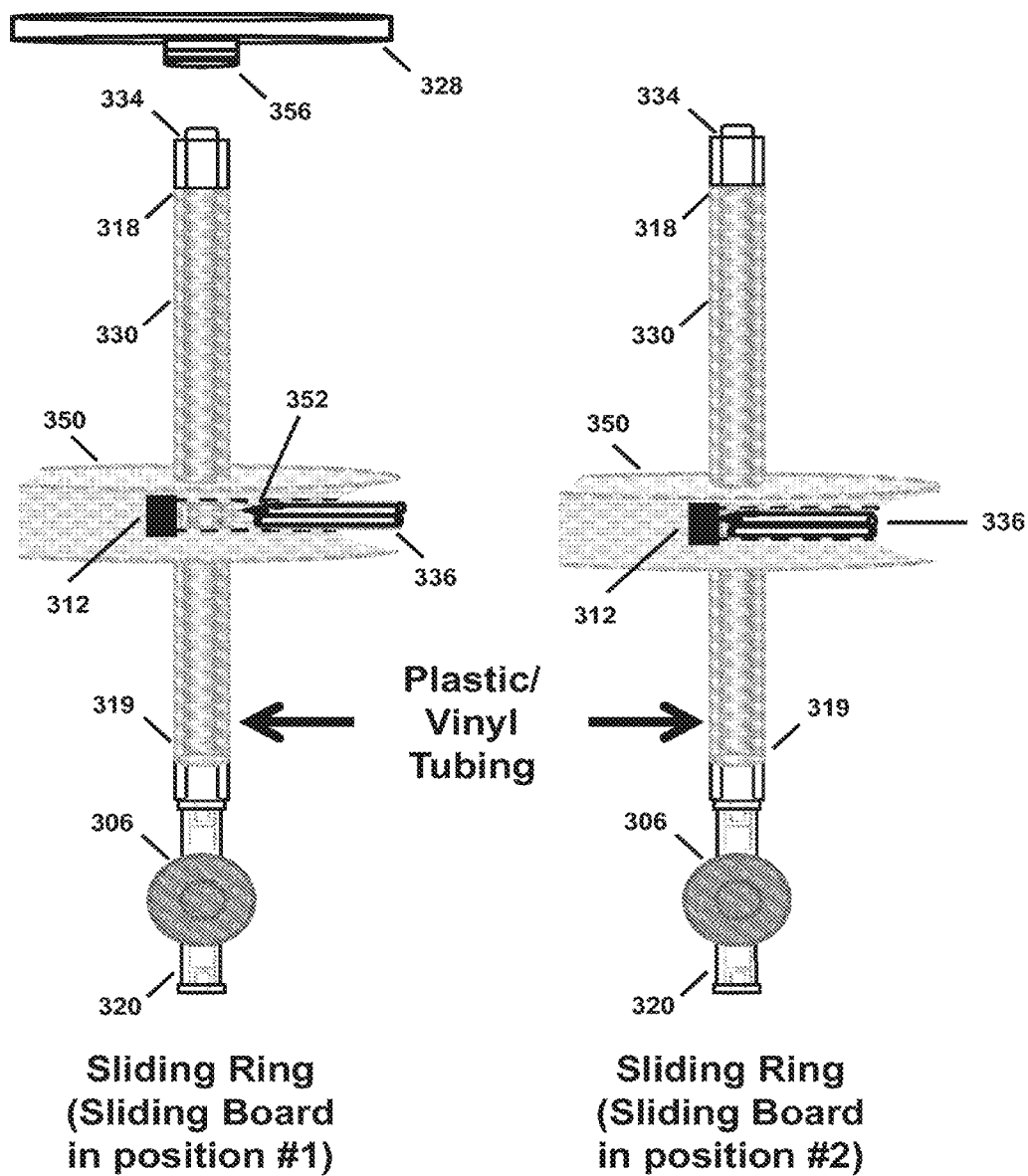
FIG. 3G — Sliding Ring (Sliding Board in position #1)
FIG. 3H — Sliding Ring (Sliding Board in position #2)

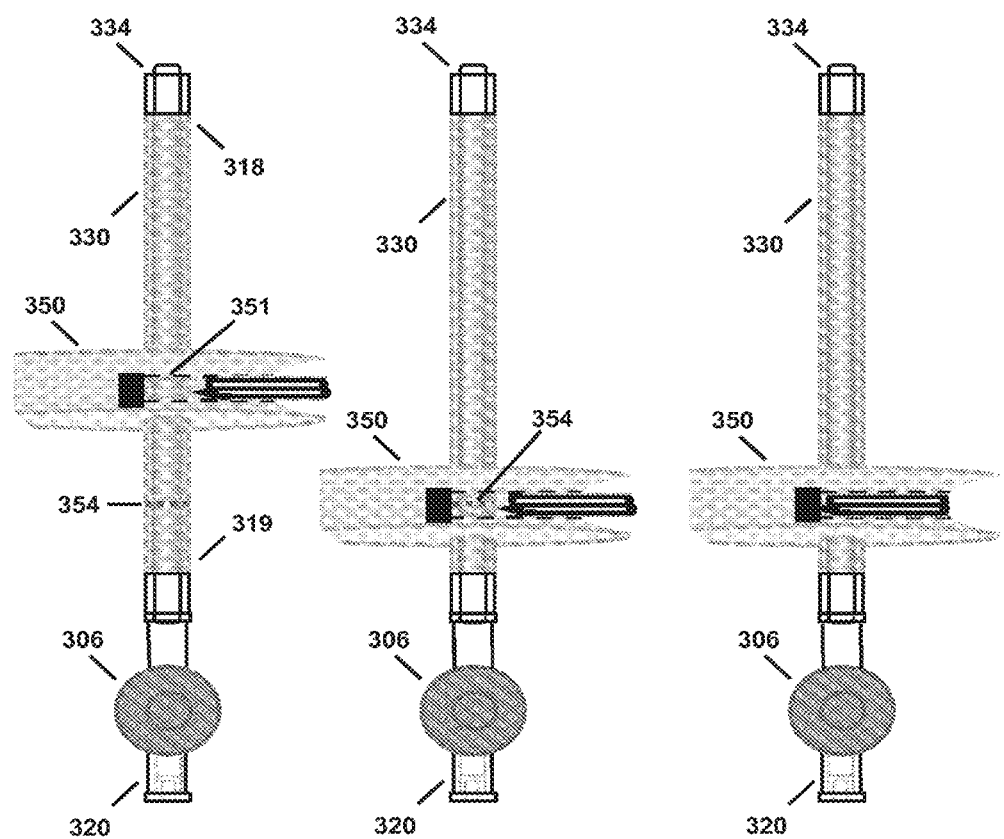

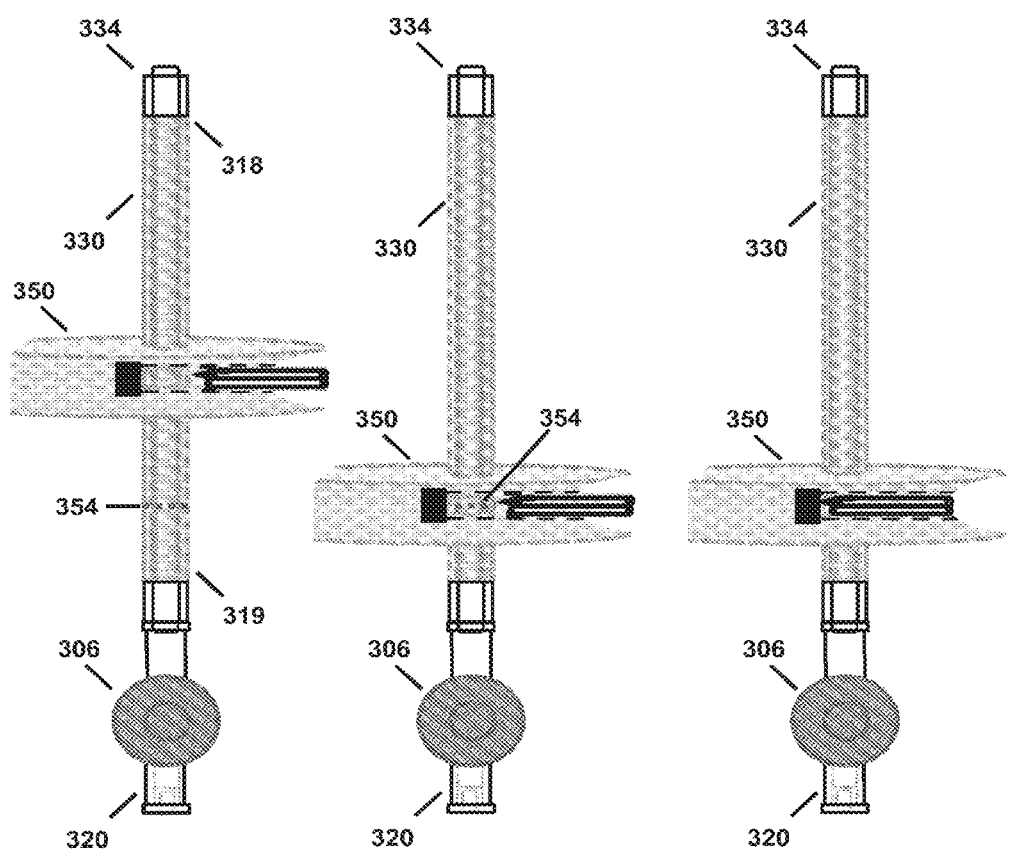

US 9,764,079 B2

METHODS AND APPARATUS FOR ISOLATION OF WHITE BLOOD CELLS USING A MULTIPOSITION VALVE

CROSS REFERENCE TO RELATED APPLICATIONS

This Application is a 35 U.S.C. §371 National Phase Entry Application of International Application No. PCT/US2013/036353 filed Apr. 12, 2013, which designates the U.S., and which claims the benefit under 35 U.S.C. §119(e) of U.S. Provisional Application No. 61/623,251 filed Apr. 12, 2012, the contents of each of which are incorporated herein by reference in their entirety.

FIELD OF THE INVENTION

The invention relates to isolation of specific cell types from bodily fluids and, more particularly, to the isolation of white blood cells from whole blood.

BACKGROUND OF THE INVENTION

White blood cells ("WBC"), also referred to as leukocytes, aid the human body in fighting infectious diseases by defending against foreign materials, such as bacteria and viruses. White blood cells play an essential role in the natural defense system, which is provided by the immune system of the human body. The number or ratio of white blood cells in the body is often used as a diagnostic of disease. For example, a consistently high number of white blood cells in the body is a strong indicator or symptom of Leukemia, a blood cancer. White blood cells are useful in a variety of medical fields, including immunology, cancer research, and other fields.

In both human and animal blood, white blood cells are mixed with other components, such as red blood cells ("RBC"). Therefore, there is a need to isolate or separate the white blood cells from the other ingredients in the blood. Current methods for the isolation of white blood cells from bodily fluids continue to be cumbersome. In general, the blood sample is mixed with an anticoagulant (e.g., EDTA), centrifuged, the plasma is removed, and the buffy coat (which forms a thin layer on top of the RBCs) is transferred to another tube and used. Under these conditions, the buffy coat contains the white blood cells as well as low levels of contaminating red blood cells and platelets. Alternatively, various red blood cell lysing buffers are added to the blood sample and the sample is centrifuged. While the latter procedure leads to the rupture of most of the red blood cells present, the non-lysed RBCs no longer sediment faster than the white blood cells and are found above the white blood cells in the centrifuge tube.

Oftentimes, such red blood cell contaminated white blood cell preparations negatively affect the downstream usage of white blood cells. For example, >99% of the cellular blood fraction is composed of red blood cells. While mature RBCs lose their nuclei and various organelles during maturation and thus do not contribute any RNA to the total RNA pool, immature RBCs (known as reticulocytes) often contain residual nucleic acids. Since ~1% of RBCs are reticulocytes, residual RNA (mostly globulin mRNA) from these cells contributes ~70% of the RNA in the total blood RNA pool. Globin mRNA can compromise the detection of other specific mRNAs from leukocytes. Heme is also present at relatively high concentrations in RBCs. If heme is not adequately removed during RNA isolation of WBCs, it too can significantly impair downstream analyses such as microarray analysis and RT-PCR. Therefore, there is a strong need in the art for a process that rapidly isolates white blood cells from bodily fluids that are void of red blood cell contaminations.

SUMMARY OF THE INVENTION

The object of the present invention is to solve the problems with the conventional prior art techniques and to provide apparatus and methods for the rapid isolation of white blood cells that are practically void of contaminating red blood cells, i.e., from an RBC:WBC ratio of 1,000:1 down to <10:1.

In one aspect of the present invention, a method for isolating white blood cells from blood is provided and comprises the acts of adding a blood sample to a separation tube having a distal end, a proximal end, and a valve located proximate said proximal end, said valve being configured to transition between at least first and second positions and removably attaching a cap to the distal end and centrifuging the separation tube. The method further comprises the acts of removing the cap at the distal end of the separation tube and removably attaching a first syringe to the proximal end, switching the valve to the second position, withdrawing, via the first syringe, a red blood cell sediment and switching the valve to the first position and removing the first syringe. The method further comprises the acts of adding a small volume of buffer to the separation tube, removably attaching a cap to the distal end and centrifuging the separation tube, removing the cap at the distal end of the separation tube and removably attaching a second syringe to the proximal end and switching the valve to the second position. The method further comprises the acts of withdrawing the remaining red blood cell sediment via the second syringe and switching the valve to the first position and removing the second syringe.

In another aspect of the present invention, a method for isolating white blood cells from blood is provided and comprises the acts of adding a blood sample to a separation tube having a distal end, a proximal end, and a valve located proximate said proximal end, said valve being configured to switch between at least first and second positions and adding a red blood cell lysing buffer to said blood sample and mixing said buffer with said blood sample. The method further comprises the acts of removably attaching a cap to the distal end and centrifuging said separation tube, removing the cap at the distal end of the separation tube and removably attaching a first syringe to said proximal end, switching said valve to said second position and withdrawing a white blood cell sediment via said first syringe.

In yet another aspect of the present invention, a method for isolating white blood cells from blood is provided and comprises the acts of adding a blood sample to a centrifuge tube and centrifuging the centrifuge tube, aspirating most of a plasma layer, and removing a buffy coat containing a red blood cell and white blood cell mixture. In further aspects, in accord with other concepts related to those above, the method may comprise the acts of suspending the buffy coat in buffer and adding it to a separation tube having a distal end, a proximal end, and a valve located proximate said proximal end, said valve being configured to transition between at least first and second positions, removably attaching a cap to the distal end and centrifuging the separation tube. The method may further comprise the acts of removing the cap at the distal end of the separation tube and removably attaching a first syringe to the proximal end, switching the valve to the second position, withdrawing, via the first syringe, a red blood cell sediment and switching the valve to the first position and removing the first syringe. The method may further comprise the acts of removably attaching a second syringe to the proximal end and switching the valve to the second position. The method may further comprise the acts of withdrawing the white blood cell sediment via the second syringe and switching the valve to the first position and removing the second syringe.

In yet another aspect of the present invention, a method for isolating white blood cells from blood is provided and comprises the acts of adding a blood sample to a centrifuge tube, adding a red blood cell lysing buffer to the centrifuge tube and mixing the blood sample with the buffer, centrifuging the centrifuge tube, aspirating most of a plasma-buffer layer, dispersing a red and white blood cell mixture in a remaining plasma-buffer layer, and providing a tubing with a proximal and a distal end, including a valve coupled to the proximal end, the valve being configured to transition between at least first and second positions. The method further comprises the acts of switching the valve to the second position, aspirating a mixture of the red and white blood cells and the remaining plasma-buffer layer into the tubing, switching the valve to the first position, optionally, removably attaching a first cap on the proximal end and a second cap on the distal end, and placing the tubing inside a centrifuge tube having an inner diameter substantially equal to a diameter of the caps, with the proximal end of the tubing being next to the proximal end of the centrifuge tube, and centrifuging the centrifuge tube bearing the connected valve, tubing, and the removably attached distal and proximal caps for a predetermined time at a predetermined rate. The method further includes acts of removing the connected valve, tubing, and two caps from the centrifuge tube, detaching the cap at the proximal end of the separation tube and removably attaching a syringe to the proximal end of the valve, switching the valve to the second position, withdrawing, via the syringe, the sedimented white blood cells, switching the valve to the first position, removing the first syringe, and dispensing the white blood cells into a suitable container.

In still another aspect of the present invention, a method for isolating white blood cells from blood is provided and comprises the acts of adding a blood sample to a centrifuge tube and centrifuging the centrifuge tube, aspirating most of a plasma layer, removing a buffy coat, providing a tubing with a proximal and a distal end, including a valve coupled to the proximal end, the valve being configured to transition between at least first, second, and third positions, and switching the valve to the second position. The method further includes the acts of aspirating a sample contained in the centrifuge tube into the tubing, switching the valve to the first position, removably attaching first cap to the proximal end and second cap to the distal end, placing the tubing inside a centrifuge tube with its proximal end of the tubing being next to the proximal end of the centrifuge tube having an inner diameter substantially equal to a diameter of the caps, with the proximal end of the tubing being next to the proximal end of the centrifuge tube, and centrifuging the centrifuge tube bearing the connected valve, tubing, and the removably attached distal and proximal caps for a predetermined time at a predetermined rate. The method further includes acts of removing the connected valve, tubing, and two caps from the centrifuge tube, detaching the cap at the proximal end of the separation tube and removably attaching a syringe to the proximal end of the valve, switching the valve to the second position, withdrawing, via the syringe, the sedimented red blood cells and switching the valve to the first position and removing the first syringe. The method may further comprise the acts of removably attaching a second syringe to the proximal end and switching the valve to the third position, withdrawing the white blood cell sediment via the second syringe, and switching the valve to the first position and removing the second syringe, and dispensing the white blood cells into a suitable container.

In yet another aspect, a method for isolating white blood cells from blood, includes the acts of introducing a blood sample into a centrifuge tube, adding a red blood cell lysing buffer to the blood sample, centrifuging the blood sample for a predetermined amount of time at a predetermined rate, aspirating most of the supernatant plasma-buffer, and dispersing the red blood cell-white blood cell mixture in the remaining plasma-buffer. The method further includes the act of preparing a tubing assembly comprising (i) a removable syringe to a proximal end of a valve via mating connection members; (ii) a proximal end of a tubing to a distal end of the valve via mating connection members; (iii) a capped needle to a distal end of the tubing via mating connection members; and (iv) a sliding ring bearing a cutting element about the tubing, the cutting element being adapted to bias inwardly against the tubing, the valve having at least a first closed position and a second open position. The act of preparing may comprise either removably connecting one or more of such components during the execution of the method or preparing a pre-assembled assemblage of such components or partially pre-assembled assemblage of such components. The method further includes acts of setting the valve in the second position, uncapping the needle, using the syringe to aspirate into the tubing, from the centrifuge tube, the red blood cell-white blood cell and plasma-buffer sample, capping the needle, and setting the valve in the first position. The method further includes acts of detaching the capped needle, capping the distal end of the tubing with a cap via mating connection members, disposing the connected valve, capped tubing, and sliding ring into a centrifuge tube having an inner diameter substantially equal to a diameter of at least the sliding ring and the cap, and centrifuging the centrifuge tube bearing the connected valve, tubing, and sliding ring for a predetermined time at a predetermined rate. The method further includes acts of removing the connected valve, tubing, and sliding ring from the centrifuge tube and positioning for further processing, and removably attaching a syringe, via a mating connection member, to the proximal end of the valve that is closest to the white blood cell portion of the interphase. The method further includes acts of sliding the sliding ring toward the location of the interphase, determining a location of the interphase between the white blood cell and red blood cell layer, positioning the sliding ring at the interphase and actuating the sliding board to bias the cutting element against the tubing and through the tubing to bisect the tubing at the interphase so as to separate the tubing into a first part proximal to valve that includes the white blood cells and a second part that includes the red blood cells. The method optionally includes the further acts of positioning an opening of an air tunnel component of the sliding board within the tubing and adjacent the white blood cells in the tubing, setting the valve in the second position, and using the syringe to aspirate the white blood cells from the tubing.

In yet another aspect, a method for isolating white blood cells from blood, includes the acts of introducing a blood sample to a centrifuge tube, centrifuging the sample for a predetermined amount of time at a predetermined rate, aspirating most of the plasma layer above a buffy coat layer, and removing the buffy coat layer together with some of the red blood cells present below the buffy coat layer and transferring the removed material to a clean tubing assembly. The tubing assembly comprises (i) a syringe removably attached to a proximal end of a valve via mating connection members; (ii) a proximal end of a tubing removably attached to a distal end of the valve via mating connection members; (iii) a capped syringe needle removably attached to a distal end of the tubing via mating connection members; and (iv) a sliding ring bearing a cutting element about the tubing, the cutting element being adapted to bias inwardly against the tubing, the valve having at least a first closed position and a second open position. The method further includes acts of setting the valve in the second position, uncapping the needle, using the syringe to aspirate the buffy coat from the centrifuge tube into the tubing, capping the needle, setting the valve in the first position, and detaching the capped needle. The method further includes acts of capping the distal end of the tubing with a cap via mating connection members, disposing the connected valve, tubing, and sliding ring and the cap into a centrifuge tube having an inner diameter substantially equal to a diameter of at least the sliding ring and the cap, and centrifuging the centrifuge tube bearing the connected valve, tubing, and sliding ring for a predetermined time at a predetermined rate. The method further includes acts of removing the connected valve, tubing, and sliding ring from the centrifuge tube and positioning for further processing, and removably attaching a syringe, via a mating connection member, to the distal end of the tubing that is closest to the white blood cell portion of the interphase. The method further includes acts of sliding the sliding ring toward the location of the interphase, determining a location of the interphase between the white blood cell and red blood cell layer, and positioning the sliding ring at the interphase and actuating the sliding board to bias the cutting element against the tubing and through the tubing to bisect the tubing at the interphase so as to separate the tubing into a first part proximal to valve that includes the red blood cells and a second part that includes the white blood cells. The method optionally includes the further acts of positioning an opening of an air tunnel component of the sliding board within the tubing and adjacent the white blood cells in the tubing and using the syringe to aspirate the white blood cells from the tubing.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1 is an embodiment of a white blood cell isolation system, showing a separation-centrifuge tube and its cap, two syringes, and a centrifuge tube.

FIG. 2B is a view of the setup of one syringe, a valve, the tubing unit, and the capped needle of FIG. 2A.

FIG. 2C is a view of the valve-tubing unit, capped at both ends, of FIG. 2A.

FIG. 2D is a view of the capped-valve-tubing unit of FIG. 2C inside the centrifuge tube of FIG. 2A.

FIG. 2E is the view of the capped tubing-valve unit with second syringe of FIG. 2A.

FIG. 2F is a view of the three valve positions of the valve of FIG. 2A.

FIGS. 3A-3H depicts another embodiment of a white blood cell isolation system in accord with aspects of the present concepts, showing a centrifuge tube and its cap (FIG. 3A), a valve (FIGS. 3C-3D), a syringe (FIG. 3B), a capped needle (FIG. 3B), and a tubing cap (FIG. 3E), a tubing-valve and a sliding ring unit with the blade positioned proximal to the valve and the sliding board in position 1 (FIG. 3E) or in position 2 (FIG. 3F), and a tubing-valve and a sliding ring unit with the blade positioned distal to the valve and the sliding board in position 1 (FIG. 3G) or in position 2 (FIG. 3H).

FIG. 5C is another view of the tubing unit with the sliding ring of FIG. 3 with its blade positioned proximal to the valve and its sliding board in position 1 as shown in FIG. 4A.

FIG. 5D is yet another view of the tubing unit with the sliding ring of FIG. 5C positioned at the WBC-RBC interface and its sliding board in position 1 as shown in FIG. 4A.

FIG. 5E is yet another view of the tubing unit in which the sliding board of the sliding ring of FIG. 5D in position 2 as shown in FIG. 4B.

FIG. 6C is another view of the tubing unit with the sliding ring of FIGS. 3A-3H with its blade positioned distal to the valve and its sliding board in position 1 as shown in FIG. 4A.

FIG. 6D is yet another view of the tubing unit with the sliding ring of FIG. 5C positioned at the RBC-WBC interface and its sliding board in position 1 as shown in FIG. 4A.

FIG. 6E is yet another view of the tubing unit in which the sliding board of the sliding ring of FIG. 6D in position 2 as shown in FIG. 4B.

DETAILED DESCRIPTION

Figure 2A:
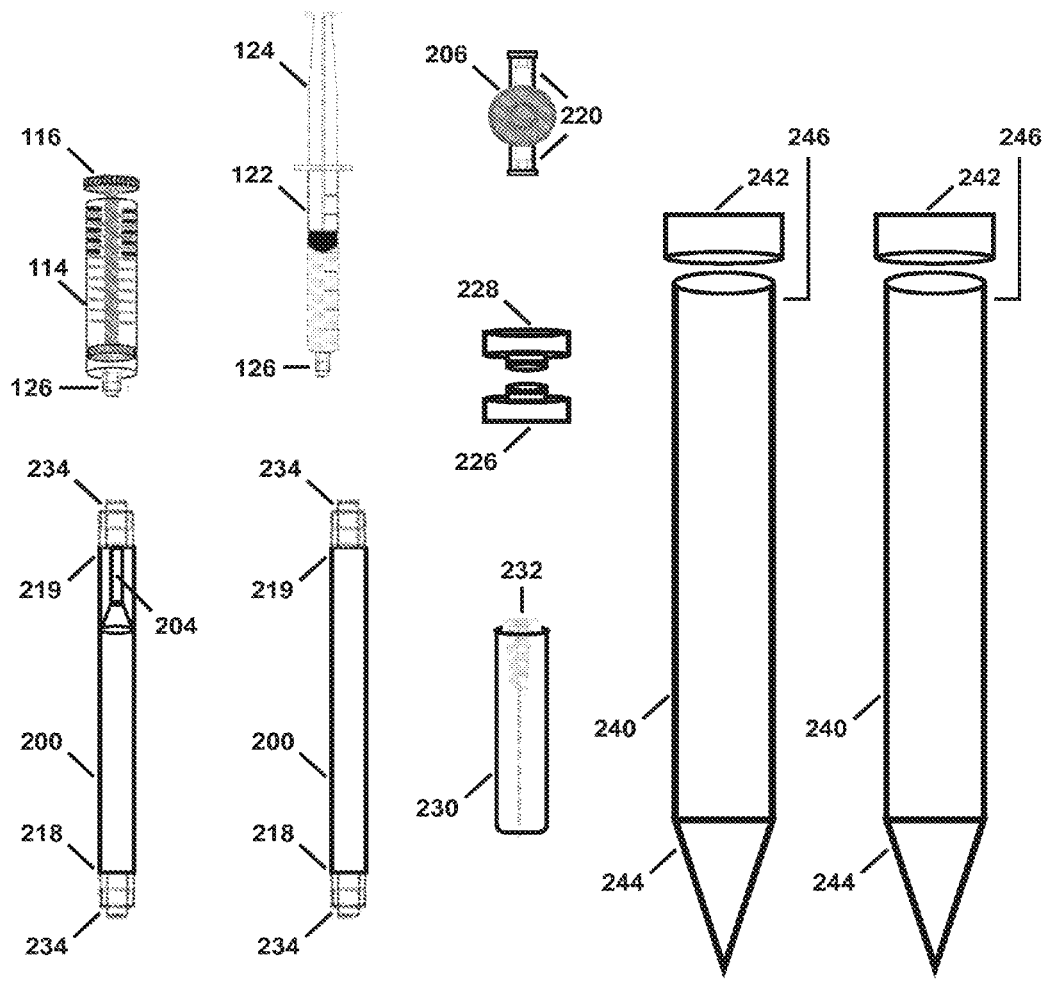
FIG. 2A is another embodiment of a white blood cell isolation system, showing a centrifuge tube and its cap, two tubing units and their two caps, a valve, two syringes, and a capped needle.

Although the invention will be described in connection with certain illustrative examples and preferred embodiments, it will be understood that the invention is not limited to those particular embodiments. On the contrary, the invention is intended to cover all alternatives, modifications, and equivalent arrangements as can be included within the spirit and scope of the invention as disclosed herein and as represented by the appended claims.

The white blood isolation kit of the present invention allows a user to rapidly isolate white blood cells practically free of red blood cells or other contaminants. FIG. 1 is a perspective view of a white blood cell isolation kit according to one embodiment of the invention. The kit illustrated in FIG. 1 includes a separation tube 100 comprising a distal end 118 and a proximal end 120. Optionally, a cap 102 can be detachably or removably coupled to the distal end 118 of the separation tube 100. In one aspect, the cap 102 comprises a threaded portion that is configured to securely engage a correspondingly threaded portion on the distal end 118 of the separation tube 100. Alternatively, other conventional means of engagement between the cap 102 and the tube 100 can be utilized to isolate or seal the distal end 118 of the separation tube 100. The separation tube 100 additionally includes a neck section 104 which is located between the proximal end 120 and the distal end 118. As depicted in FIG. 1, the neck 104 is situated proximate the proximal end 120 of the separation tube 100. The separation tube 100 can be in the form of a centrifuge tube or can be adapted to fit inside a centrifuge tube and can be constructed from one or more materials including plastic, glass, vinyl, or other suitable materials.

In various aspects, the separation tube 100 can comprise a valve 106, as shown in FIG. 1, or can comprise a connector configured for connection to a valve 106. The valve 106 can have at least two and, preferably, at least three operative positions. FIG. 1 depicts a 4-way valve 106. When the valve 106 is in the first position 108, no bodily fluid components can flow out of the proximal end 120 of the separation tube 100. In the first position 108, the proximal end 120 is effectively closed or sealed. Preferably, in position 108, the valve 106 maintains the proximal end 120 sealed during centrifugation. When the valve is in a second position 110, bodily fluid components can flow from or be drawn out of the separation tube 100. For example, the bodily fluid components can be drawn from the separation tube via a syringe 122 or 114, or via any other suction-type device. The syringe 122 or 114 can be removably coupled via its male luer 126 to the separation tube 100 via a female luer 128 that is configured to removably couple to a male luer connection of the syringe 122 or 114 so that bodily fluids can be safely and easily withdrawn from the proximal end 120. In one presently preferred aspect, the valve can include a plurality of separate passages so that fluids passed by the valve in one position do not flow through the same passage as fluid passed by the valve in another position. For example, in the second position 110, the bodily fluid components can be drawn through a first passage through valve 106 that is separate from any other passage(s) through valve 106. Correspondingly, in the third position 112, described below, the bodily fluid components can be drawn through a second passage through valve 106 that is separate from, for example, the first passage. Other removable connection means between the syringe 122 or 114 to the separation tube 100 are optionally implementable in accord with other aspects of the present concepts and can include, without limitation, a threaded connection.

The valve 106 can also have a third position 112; when the valve is in the third position 112, bodily fluid components can flow out of the separation tube 100 and withdrawn from the separation tube 100 via a syringe or another suction-type device. The kit can also include a syringe 122, which can be any type of syringe that is known in the art. In one aspect, the syringe 122 comprises a large syringe with a capacity to hold 1-50 mL of fluids and the syringe includes a plunger 124 configured to be pulled to thereby draw a sample. The kit can also or alternatively include a syringe 114 comprising a rotation or "screw-type" plunger 116 wherein the plunger 116 of the syringe 114 is rotated to withdraw the plunger seal and precisely draw a sample of a desired volume. According to one embodiment, the syringe 114 is a mini syringe, configured to hold 0.1-2 mL of fluid. In at least some presently preferred aspects, the syringe 114 enable the gentle, slow, and precise withdrawal of the sedimented WBC pellet with minimal disturbance.

According to one embodiment of the invention, a process to isolate white blood cells comprises removal of the cap 102 from the separation tube 100 and verification that the valve 106 is in the first position 108 to ensure isolation of the proximal end 120. With the valve 106 in the first position 108, a blood sample is added to the separation tube 100 and the cap 102 is then removably attached to the distal end 118 of the separation tube 100. The sample is then centrifuged in a centrifuge for a predetermined time at a predetermined rate, or optionally at a variety of times at a variety of rates, to achieve a desired separation of the constituent components of the blood sample. By way of example, in one embodiment, the sample can be centrifuged for about five minutes at a rate of about 2,000 rpm. In another embodiment, the sample can be centrifuged for between 5-10 minutes a rate between about 500-2,500 rpm, or at one or more rates between about 500-2,500 rpm.

After centrifugation of the separation tube 100, a user is able to visually distinguish the buffy coat from the red blood cells due to color differences. Following centrifugation, three layers generally form within the separation tube 100: a red blood cell layer, a buffy coat layer, and a plasma layer. The red blood cell layer sediments to the bottom of the separation tube 100 and has a reddish color. The plasma layer is generally clear and is situated on the top of the separation tube 100. The buffy coat layer is a thin layer, generally occupying less than about 1% of the total sample volume that forms between the red blood cells and the plasma layer. The buffy coat layer contains a majority of the white blood cells and some platelets and usually has a white tint, although it may have a green tint.

Thus, the centrifugation causes the red blood cells to sediment to the bottom of the separation tube 100, i.e., to the proximal end 120 and the plasma situated on top of the buffy coat, i.e., at the distal end 118. The cap 102 is then loosened and removed and a clean Pasteur pipette (not shown) or the like is used to withdraw most of the plasma from the distal end 118 of the separation tube 100. A clean syringe 122 is then removably attached to the proximal end 120 of the separation tube 100, such as by inserting and rotating a male end 126 of syringe 122 into a corresponding female end 128 of valve 106. The valve 106 can then be rotated to the second position 110 (or alternatively the third position 112), and the sedimented red blood cells withdrawn from the proximal end 120 of the separation tube 100 via the syringe 122. The sample is withdrawn until the buffy coat edge is within the neck section 104 of the separation tube 100. Because the narrow neck section 104 can hold a small amount of the sample in an elongated tube, the red blood cell layer can be visualized and accurately removed; in other words, white blood cells are not removed along with the red cells. By way of example, in one non-limiting aspect of the present concepts, an internal diameter of the narrow neck section 104 is between about 1-2 mm and a length of such neck section is between about 3 mm-2 cm.

After withdrawing the red blood cells layer, the valve 106 is rotated to the first position 108 to isolate the distal end 118 of the separation tube 100 and the syringe 122 is removed. A small volume of buffer, for example phosphate buffer saline (PBS), is then added to the volume remaining the separation tube 100, the cap 102 secured to the proximal end of the separation tube, and the separation tube 100 rotated several times to mix its contents and the tube can be centrifuged for an additional suitable period of time. The user can, for example, centrifuge the sample for five minutes at 2000 rpm. The remaining red blood cells sediment to the proximal end 120 of the separation tube 100. The syringe (e.g., syringe 114) is then attached to the proximal end 120, the valve 106 is rotated to the same position as previously used for withdrawing the red blood cells layer (e.g., second position 110), and the cap 102 loosened to thereby permit fluid to be withdrawn from the proximal end 120 of the separation tube 100. The remaining red blood cells layer is then able to be withdrawn via the syringe. A syringe 114 equipped with a rotation plunger 116 is particularly advantageous because it effectively controls the rate at which a sample can be withdrawn from the separation tube 100. Every degree of rotation of the plunger 116 permits a predetermined, small amount of the sample to be taken out and, correspondingly, each full rotation precisely draws a predetermined amount of the sample. After withdrawing the remaining red blood cells sediment, the valve 106 is rotated to the first position 108 and the syringe 114 is removed. The separation tube now contains pure or substantially pure (e.g., greater than or equal to about 98%) white blood cells. A clean syringe 114 (not shown) is then removably attached to the proximal end 120, the valve is rotated to the third position 112 (or alternatively the second position 110 if the third position was previously used for the red blood cells layer), and the white blood cells withdrawn via the clean syringe. The withdrawn white blood cells contain a minimal amount of plasma and/or plasma-PBS mixture. The valve can then be rotated to the first position 108 and the syringe containing the white blood cells is removed. The white blood cells with the minimal amount of plasma-PBS can then be dispensed from the syringe into any suitable container, such as a test tube, plate, etc., for use in a variety of downstream applications.

In at least some aspects, the valve 106 is a four-way valve with three distinct positions 108, 110, and 112. The valve 106 is optionally, but preferably, translucent. The use of a four-way valve has a variety of benefits, including preventing cross-contamination of the white blood cells by the red blood cells. The red blood cells can be withdrawn only when the valve 106 is in the second position 110 and, thus, the red blood cells only come into contact with the port of the valve 106 that is exposed when the valve 106 is in the second position. The white blood cells, on the other hand, can be removed when the valve is in the third position 112. The port through which the white blood cells are withdrawn is therefore clean; no red blood cells or other material is removed through that port.

According to yet another aspect of the present concepts, a blood sample is added to the separation tube 100, following removal of the cap 102 and positioning of the valve 106 in the first position 108. A red blood cell lysing buffer is then added to the blood sample and the cap 102 then detachably coupled to the distal end 118 of the separation tube 100, following which the blood sample and the lysing buffer are gently mixed. The lysing buffer can be any buffer configured to lyse red blood cells from blood. Once most of the red blood cells have lysed, usually within about 2-3 minutes, the separation tube 100 containing the sample is centrifuged, preferably for a predetermined period of time sufficient to achieve a desired separation of the white blood cells and red blood cells, with the intervening buffy coat layer. By way of example, the separation tube 100 is centrifuged for about five minutes at 2000 rpm, but other combinations of time periods and/or rates may be utilized to achieve the separation described herein.

As noted above, the centrifugation causes the white blood cells to sediment to the proximal end 120 of the separation tube 100. Red blood cells in whole blood sediment faster than the white blood cells, leading to the white blood cells/buffy coat being situated above the sedimented red blood cells. However, after the addition of a red blood cell lysing buffer, the white blood cells are found below the red blood cells that have not lysed.

Continuing with the above example wherein the red blood cell lysing buffer is added to the blood sample, the valve 106 is switched to the second position 110 (or alternatively the third position 112), and the cap 102 loosened. The sedimented white blood cells-plasma-buffer layer is then withdrawn, making sure that no red blood cells are drawn into the white blood cell sample. As noted above, withdrawal of the white blood cells-plasma-buffer layer is preferably performed using a syringe 114 comprising a screw-like plunger 116 that moves by rotation in order to more precisely control the rate of white blood cell removal and to prevent contamination by red blood cells. The white blood cells-plasma-buffer layer is then able to be dispensed into a suitable container.

According to still another embodiment of the present disclosure, a blood sample can be added to a centrifuge tube (not shown) and the sample centrifuge, such as is described above. Most of the plasma layer that is formed above the buffy coat can then be aspirated using any acceptable method such as by using, for example, a Pasteur pipette (not shown). The buffy coat can then be removed, along with some of the red blood cells present below the buffy coat. The buffy coat and the red blood cells can then be transferred to a clean separation tube 100, with the valve 106 being in the first position 108. The separation tube 100 can then be filled with PBS, culture media, or any other suitable fluid. The cap 102 can then be removably attached to the distal end 118, the contents mixed by gentle rotation of the tube, and the tube can be centrifuged for an acceptable time at an acceptable rate, such as, for example, 5 minutes at 2000 rpm. The centrifugation causes the remaining red blood cells to sediment towards the proximal end 120 of the separation tube 100. A syringe 114 can then be removably attached to the proximal end 120 and the valve 106 switched to the second position 110 (or alternatively the third position 112 if desired). The cap 102 is then loosened and the remaining sedimented red blood cells withdrawn by rotating the screw-like plunger 116 of syringe 114. Alternatively, other types of syringes (e.g., syringe 122) could be used. The valve 106 can then be switched back to the first position 108 to isolate the separation tube 100. The red blood cell-containing syringe 114 can then be removed and a clean syringe 116 (not shown) is removably attached to the proximal end 120 of the separation tube 100. The valve 106 is then switched to the third position 112 (or alternatively the second position 110 if the third position was previously used for withdrawal of red blood cells) and the white blood cells along with a minimal volume of plasma can be withdrawn. The valve is then switched to the first position 108, and the syringe removed. The white blood cells with the minimal volume of plasma can then be dispensed from the syringe into any acceptable container.

Referring now to FIG. 2A, a white blood isolation kit in accord with at least some aspects of the present concepts comprises a syringe 122, which can be any type of syringe that is known in the art, syringe 114 which can include a rotation or "screw-type" plunger 116, a needle 232 that is capped 230, a valve 206 that has two female luer connections 220, two centrifuge tubes 240 that each have a distal end 246 and a proximal end 244, and two caps 242 configured to be detachably coupled to the distal end 246 of centrifuge tube 240. The cap 242 can be a screw cap or any other cap configured to close access to the distal end 246 of the centrifuge tube 240. The centrifuge tube 240 can be made from, for example, plastic, glass, vinyl, or any other suitable biocompatible material.

The kit represented in FIG. 2 additionally is shown to include tubing 200 comprising a distal end 218 connected to or integrated with a male luer 234 and a proximal end 219 that is also connected to or integrated with a male luer 234. The tubing 200 additionally can include a neck section 204 located between the proximal end 219 and the distal end 218. The neck 204 can be situated, in one aspect, proximate the proximal end 219 of the tubing 200. The tubing 200 can be manufactured out of plastic, glass, vinyl, or any other suitable transparent or semi-transparent material. The tubing 200 can also include a narrower portion at its distal end 218 than at its proximal end 219. The tubing 200 can have a diameter ranging from approximately 0.5 mm to approximately 5 mm. The presently preferable range for the tubing 200 diameter is between approximately 1 mm to approximately 2 mm. The male luer 234 at the proximal end 219 of tubing 200 is configured to be detachably coupled to the female luer 220 of valve 206. A cap 228 can then be detachably coupled to the other female luer 220 of valve 206. Additionally, the other male luer 234 at the distal end 218 of tubing 200 can be detachably coupled to the female luer 220 of cap 226. The caps 226 and 228 can be any type of caps that are configured to close access to the tubing 200 and valve 206 such that no fluid may flow out of the tubing 200, such as is shown by way of example in FIG. 2C. In at least some aspects, the caps 226 and 228 have an external diameter that is substantially equal to the internal diameter of the centrifuge tube 240 so that the caps 226, 228 facilitate the positioning of and securement of the tubing 200 inside the centrifuge tube 240, such as is shown in FIG. 2D.

Referring now to FIGS. 2A-2B, the capped needle 232 is detachably coupled to the male luer 234 at the distal end 218 of tube 200 and the other male luer 234 at the proximal end 219 of tube 200 is detachably coupled to a female luer 220 of valve 206, and the male luer 126 of syringe 122 is detachably coupled to the other female luer 220 of valve 206. This capped needle-tubing-valve-syringe can be used to withdraw blood or buffy coat preparations or WBC preparations after RBC lysis into the tubing and used for the isolation of WBCs.

Referring now to FIGS. 2A and 2C, the cap 226 is detachably coupled to the male luer 234 at the distal end 218 of tubing 200 so as to block the flow of any liquid within the distal end of the tubing 200. Similarly, the cap 228 is detachably coupled to the female luer 220 of valve 206, attached to the proximal end 219 of tubing 200 so as to block the flow of any liquid within the proximal end of the tubing 200. Since the caps 226 and 228 can have an external diameter that is substantially equal to or equal to the internal diameter ("ID") of the centrifuge tube 240 and the length of the cap-valve-tubing-cap setup can be substantially equal to or equal to the length of the centrifuge tube 240, the setup shown in FIG. 2C can be inserted into centrifuge tube 240, as is shown in FIG. 2D.

Referring now to the example of FIGS. 2E-2F, the valve 206 can have at least three positions. When the valve 206 is in the first position 208, shown in FIG. 2F, no bodily fluid components can flow out of the proximal end 219 of the tubing 200. In the first position 208, the proximal end 220 is effectively sealed. When the valve 206 is in the second position 210, bodily fluid components can flow out of the tubing 200, or, alternatively, such bodily fluid components can be withdrawn from the tubing 200 via a syringe 122 or 114, or via any other suction-type device. The valve 206 can also have a third position 212, comprising a flow path separate from the flow path associated with the second position 210, in which bodily fluid components can flow out of the tubing 200 or can be withdrawn from the tubing via a syringe or another suction-type device.

According to one embodiment of the present concepts, a blood sample can be added to a centrifuge tube 240. Any suitable red blood cell lysing buffer can then be added to the centrifuge tube 240 and the components can be mixed gently. Once most of the red blood cells have lysed, the sample can be centrifuged for a suitable time period at a suitable rate, for example, for five minutes at 2000 rpm. After the centrifugation, most of the supernatant plasma-buffer can be aspirated and the red blood cell and white blood cell mixture within the pellet is then dispersed in the remaining plasma-buffer. The WBCs are not lysed by the lysing buffer while most of the RBCs are. Consequently, the small cell pellet that sediments at the bottom of the centrifuge tube consists of the WBCs and the very small fraction (e.g., <0.1% of the original RBC present) of the RBCs that did not rupture. The RBC ghosts (cell membranes) do not sediment during the centrifugation and are removed when the plasma-buffer is decanted.

In this embodiment of this WBC isolation system, the valve 206 in the capped needle-tubing-valve-syringe setup shown in FIG. 2B can be switched to open access 210 or 212 (as shown in FIG. 2F) such that fluid may flow out of the tubing 200. The cap 230 of needle 232 is removed, and the needle is inserted in the tube containing the RBC-WBC-plasma-buffer mixture isolated above, and the plunger 124 in syringe 122 used to aspirate the sample into the tubing 200. The valve 206 can then be rotated to the first position 208, the needle 232 can be capped, and the setup shown in FIG. 2B can then be flipped 180°. The syringe 122 can be removed, and the needle 232 can be capped and removed. A cap 228 can then be removably attached to female luer 220 of valve 206 and a cap 226 can then be removably attached to the distal end 218 of tubing 200, as shown in FIG. 2C. The capped tubing 200 can be placed inside the centrifuge tube 240 as shown in FIG. 2D and the centrifuge tube capped and centrifuged for an acceptable period of time at an acceptable rate, for example for five minutes at 2000 rpm. The caps 226 and 228 ensure that the tubing 200 is held within the center of the centrifuge tube 240. The tubing 200 can then be taken out of the centrifuge tube 240, the cap 228 can be removed, and a syringe 114 can then be removably attached to valve 206 that is attached to the proximal end 219 of the tubing 200 as shown in FIG. 2E. The valve 206 can then be switched to the second position 210, the cap 226 can be loosened and the sedimented white blood cell layer can be withdrawn using the syringe 114 by rotating the screw-like plunger 116. Once all the WBCs are in the syringe and the RBCs are still within valve 206, the valve 206 can then be switched to the first position 208. The white blood cell sample, which may contain plasma and buffer, can then be dispensed from the syringe 114 into any suitable container for downstream use.

According to another embodiment, a blood sample can be added to a centrifuge tube 240. A cap 242 can be removably attached to the distal end of the centrifuge tube 240, such as is represented in FIG. 2D. The sample can be centrifuged for a suitable time period at a suitable rate, for example, for five minutes at 2000 rpm. After the centrifugation, most of the supernatant plasma-buffer layer that is formed above the buffy coat can then be aspirated by using any acceptable method, for example using a pipette (not shown). The buffy coat can then be removed, along with some of the red blood cells present below it. The buffy coat and the red blood cells can then be transferred to a clean tube (not shown). In this embodiment of this WBC isolation system, the valve 206 in the capped needle-tubing-valve-syringe setup shown in FIG. 2B can be configured to open access 210 or 212 (as shown in FIG. 2F) such that fluid may flow out of the tubing 200. The cap 230 of needle 232 is removed, the needle is inserted in the tube containing the buffy coat (RBCs, WBCs, some platelets, some plasma, and buffer) isolated above, and the plunger 124 in syringe 122 used to aspirate the sample into the tubing 200. The valve 206 can then be rotated to the first position 208, the needle 232 can be capped, and the setup shown in FIG. 2B can then be flipped 180°. The syringe 122 can be removed, and the needle 232 can be capped and removed. A cap 228 can then be removably attached to female luer 220 of valve 206 and a cap 226 can then be removably attached to the distal end 218 of tubing 200, as shown in FIG. 2C. The capped tubing 200 can be placed inside the centrifuge tube 240 as shown in FIG. 2D and the centrifuge tube capped and centrifuged for an acceptable period of time at an acceptable rate, for example for five minutes at 2000 rpm. The caps 226 and 228 ensure that the tubing 200 is held within the center of the centrifuge tube 240. The tubing 200 can then be taken out of the centrifuge tube 240, the cap 228 can be removed, and a syringe 114 can then be removably attached to valve 206 that is attached to the proximal end 219 of the tubing 200 as shown in FIG. 2E. The valve 206 can then be switched to the second position 210, the cap 226 can be loosened and the sedimented red blood cell layer can be withdrawn using the syringe 114 by rotating the screw-like plunger 116. The valve 206 can then be switched to the first position 208. The red blood cell-containing syringe 114 can then be removed and a clean syringe 114 (not shown) then be removably attached to valve 206 that is attached to the proximal end 220 of the tubing 200. The valve 206 can then be switched to the second position 212 and the sedimented white blood cell layer can be withdrawn using the syringe 114 by rotating the screw-like plunger 116. The white blood cell sample, which may contain plasma and buffer, can then be dispensed from the syringe 114 into any suitable container for downstream use.

Figure 3A:
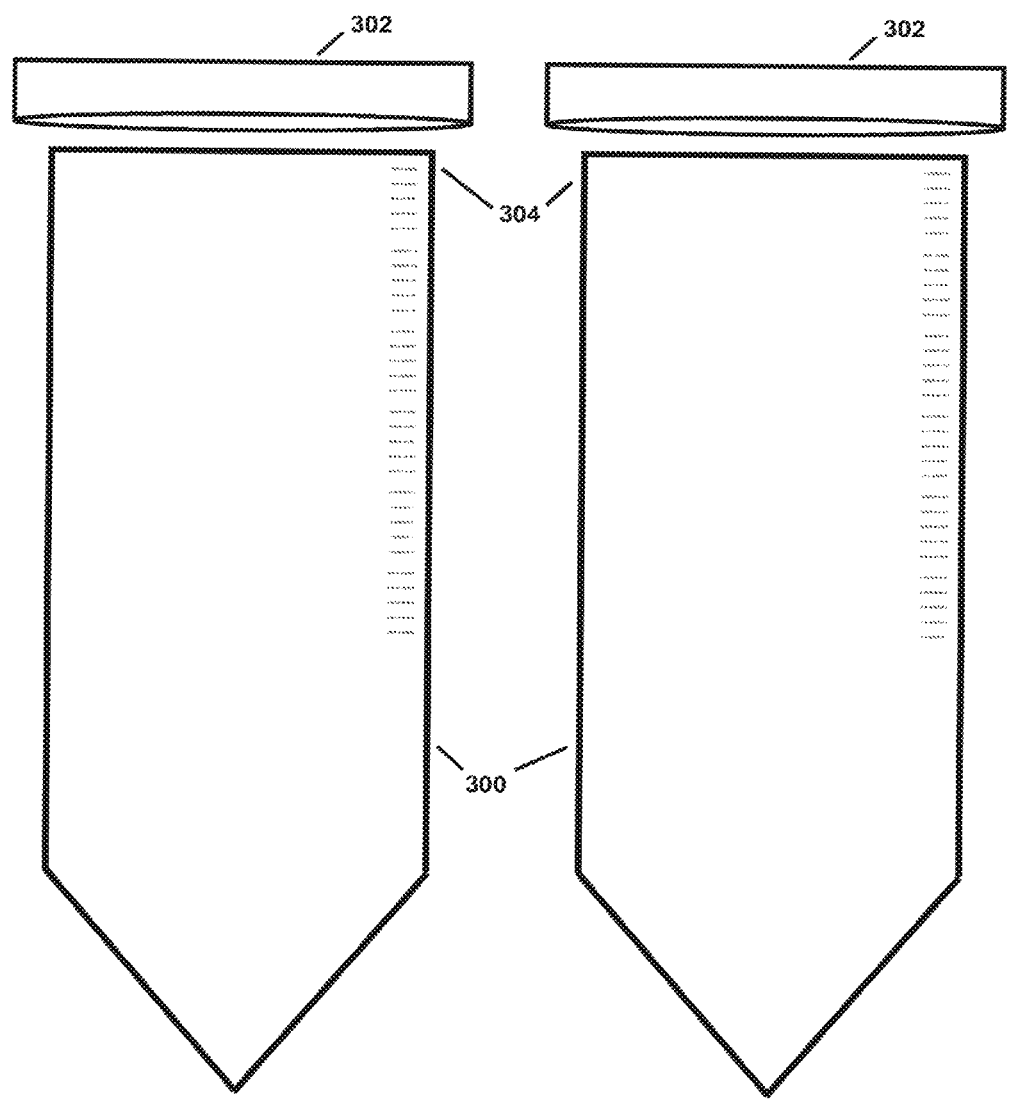

Referring now to FIG. 3A, another embodiment of the kit can include a two centrifuge tubes 300 and two caps 302, each configured to be detachably coupled to the centrifuge tube 300. The cap 302 can be a screw cap or any other cap configured to close access to the distal end 304 of the centrifuge tube 300, such that no fluid can be added to or flow out of the distal end 304. The centrifuge tube 300 can be a centrifuge tube and can be comprised of plastic, glass, vinyl, or any other suitable biocompatible material.

Figures 3B, 3C, 3D:
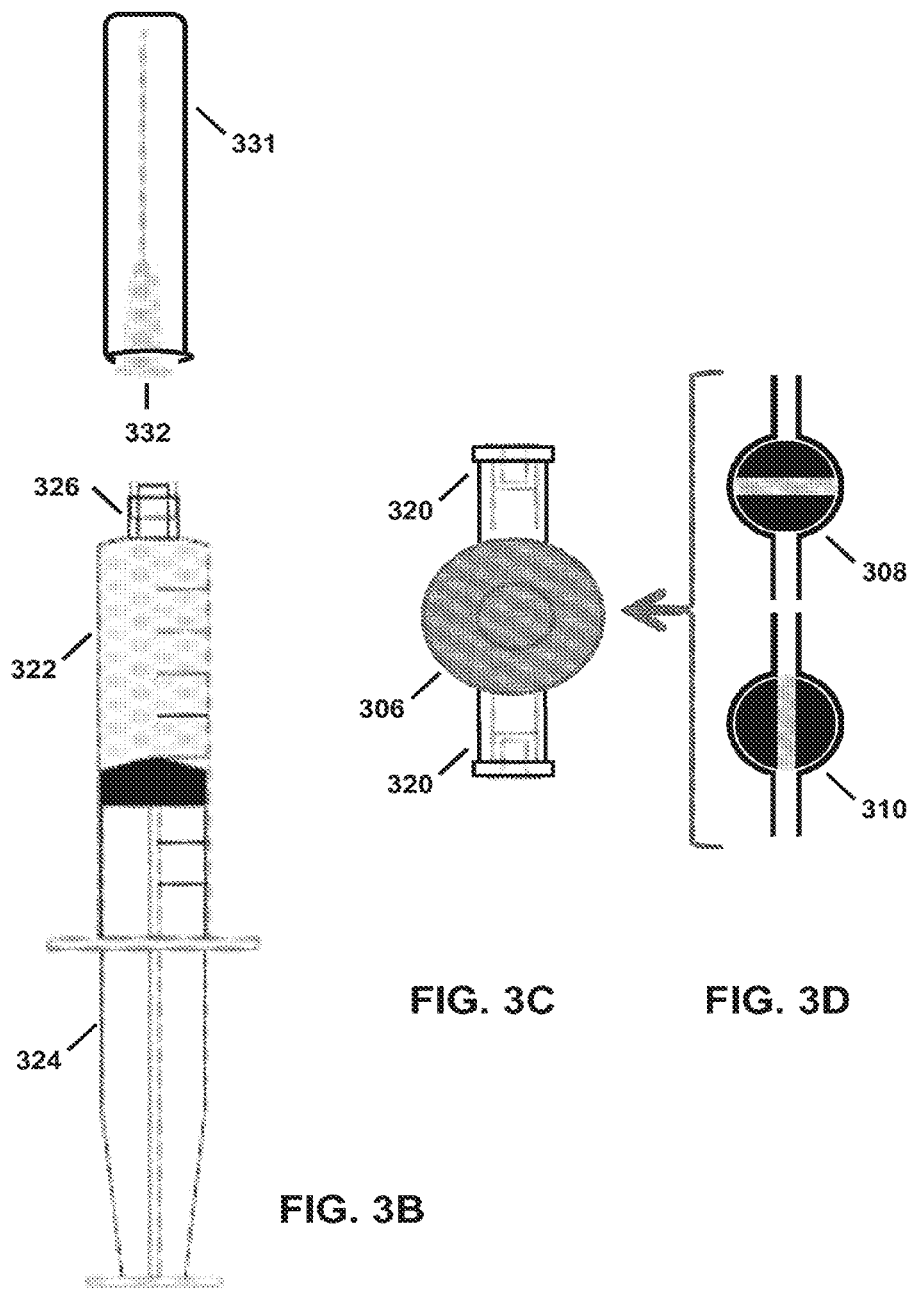

The kit can additionally include, as shown in FIG. 3B, syringe 322, which can be any type of syringe that is known in the art, a needle 332 that is capped 331, and a valve 306. The valve 306, shown in FIG. 3C, comprising two female luer connections 320, can have two positions, which are represented in FIG. 3D. When the valve 306 is in the first position 308 shown in FIG. 3D, no fluid components can flow through it and it is effectively sealed; in other words, 308 is the "closed" position. When the valve 306 is in a second position 310 shown in FIG. 3D, fluid components can flow through it; in other words, 310 is the "open" position.

The kit can additionally include, as is shown in FIGS. 3E-3H, tubing 330 that has a distal end 318 and a proximal end 319. The tubing 330 can be manufactured out of plastic, vinyl, or any other suitable transparent or semi-transparent material. The tubing 330 can have a diameter ranging from approximately 0.5 mm to approximately 10 mm. In one aspect of the present concepts, a preferable range for the tubing diameter is approximately 1 mm to approximately 3 mm.

The tubing 330 additionally includes a valve 306, as shown in FIGS. 3E-3H. The valve 306 can have two positions, for example, as shown in FIG. 3D. When the valve 306 is in the first position 308, no fluid components can flow out of the proximal end 319 of the tubing 330; in other words, 308 is the "closed" position. In the first position 308, the proximal end 319 of tubing 330 is also effectively sealed. When the valve 306 is in a second position 310, fluid components can be withdrawn from the tubing 330 via a syringe 322 or via any other suction-type device attached to a female luer 320 of valve 306; in other words, 310 is the "open" position.

As shown in FIGS. 3E-3H, a sliding ring 350 is slidably coupled to the tubing 330, such that the sliding ring 350 is configured to move along the tubing, such as from the proximal end 319 towards the distal end 318 and/or in the opposite direction. The sliding ring 350 is preferably, but not necessarily, removable. As installed, such as shown in FIGS. 3E-3H, the sliding ring 350 can be positioned in any desired location on the tubing 330 so the sliding ring cutting element 352 is adjacent a location of interest, such as but not limited to valve 306. The sliding ring 350 can be permanently attached to the tubing 330 such that it is functionally non-removable and can only be used to conduct one white blood cell isolation procedure. In other aspects, the sliding ring 350 can be constrained to slide along only a predetermined portion of the tubing 330 rather than the full extant of the tubing, such that the sliding ring is localized at a particular location of interest to achieve white blood cell isolation in accord with the concepts expressed herein.

Figure 4A:
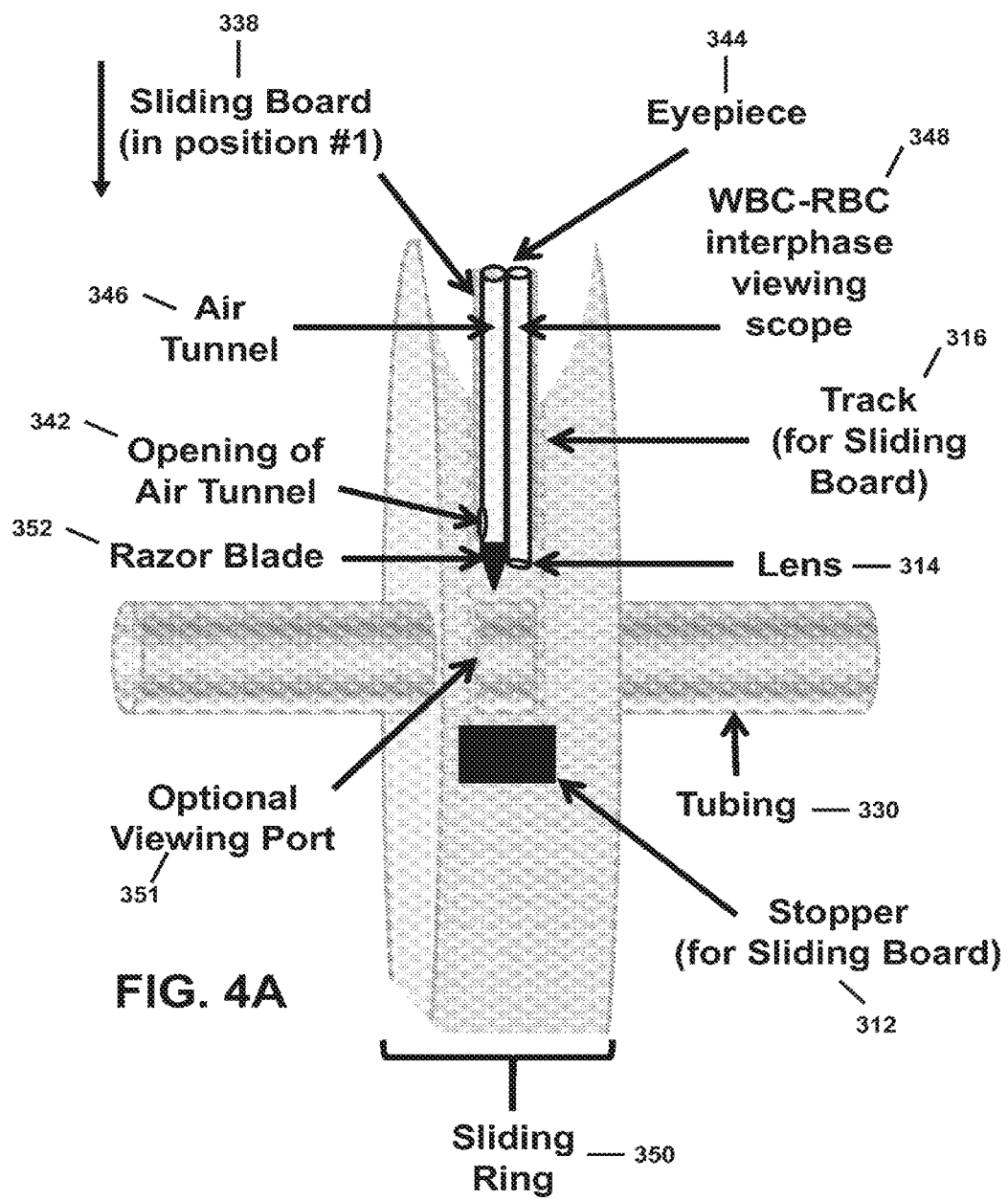
FIG. 4A is an exploded perspective view of the sliding ring of FIG. 3G with the sliding board in position 1.

In at least some aspects of the present concepts, the sliding ring 350 can include a sliding board 338 and a track 316 for the sliding board 338 (see FIG. 4A). The sliding board 338 includes a cutting element 352, an air tunnel 346, and a viewing scope 348. As is shown, for example, in FIGS. 3E-3H, and more particularly in FIG. 4A, the cutting element 352 abuts or is proximate to the external surface of tubing 330 and can be any sharp element, such as a razor, or sharp elements, configured to cut through the tubing 330. In at least one aspect, the cutting element 352 optionally defines an air tunnel 346 having a first opening 342 adjacent the cutting element, generally proximal to tubing 330, and a second opening remotely disposed from the first opening. The viewing scope 348, which is disposed adjacent the air tunnel 346, optionally abutting thereto, has an eyepiece 344 and a lens 314, the lens 314 being positioned adjacent to, or being positionable adjacent to, the cutting element 352 and proximal to the external surface of the tubing 330. The eyepiece 344 may comprise any suitable optical or solid-state (CCD array) viewing platform. The eyepiece 344 of the viewing scope 348 can be used to view the WBC-RBC interphase (see, e.g., FIGS. 5A-5E and 6A-6E) through its lens 314 that is adjacent to the cutting element 352 and proximal to tubing 330.

Figure 4B:
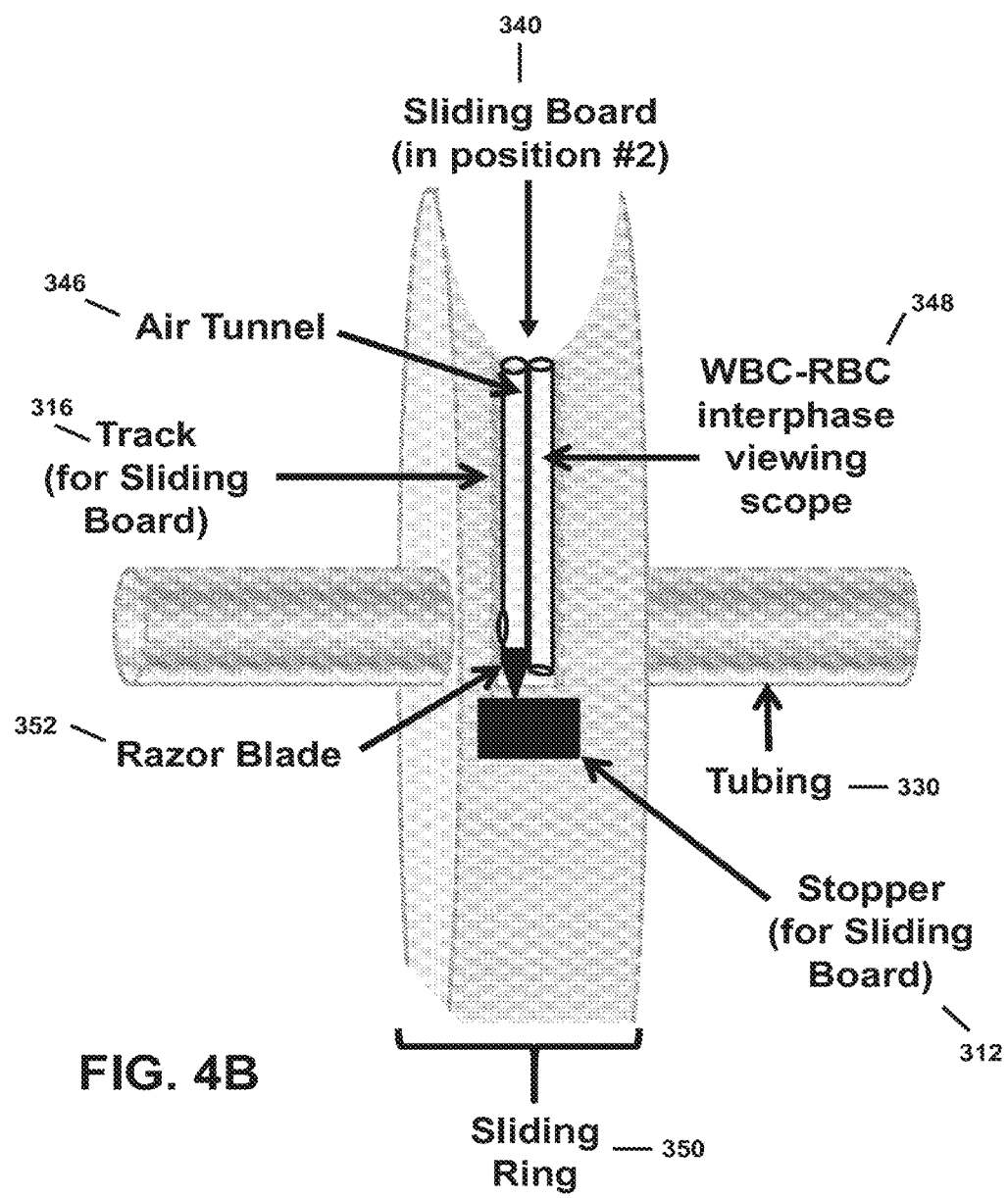
FIG. 4B is another exploded perspective view of the sliding ring of FIG. 3H with the sliding board in position 2.

The sliding board 338 shown in FIG. 4A is configured to move within track 316, represented by the dashed-lines in FIG. 4A, when an external pressure is exerted thereon, such as a pressure exerted on the proximal end of the sliding board. Under pressure applied by the operator, the sliding board 338 moves between a first position shown in FIG. 4A and a second position shown in FIG. 4B. In the first position, the cutting element 352 abuts or is proximate to the external surface of the tubing 330. The sliding board 338 can be pushed to cause the cutting element 352 to traverse through and sever the tubing 330 as shown in FIG. 4B. FIG. 4B depicts the second position of the sliding board 338, wherein the cutting element 352 has cut through the tubing 330 to rest on an optional stopper 312 disposed to inhibit or stop further motion of the sliding board 338 and cutting element 352.

The sliding board 338 may comprise the same material(s) as the sliding ring 350 or may comprise different material(s). In at least some aspects, the sliding board 338 and the sliding ring 350 comprise a POM, such as Delrin, that provides high stiffness and low friction, enabling the sliding board 338 to be moved from or between the first position (see FIG. 4a) and the second position (see FIG., 4B) within the sliding ring. In at least some aspects, the cutting element 352 and the viewing scope 348 are affixed to the sliding board 338 so that the cutting element 352 and the viewing scope 348 lens 314 are maintained in a predetermined spatial relationship. In at least one aspect, however, the cutting element 352 and the viewing scope 348 are configured for independent movement translational and/or rotational relative to one another and/or relative to the sliding board 338. In yet other aspects, the air tunnel 346 is provided separately from the cutting element 352, such as by a separate tube located adjacent the cutting blade 352 or viewing scope.

The kit additionally includes, in at least some aspects, a cap 328, such as is shown in FIGS. 3E and 3G that is configured to have a diameter that is equal to the internal diameter of centrifuge tube 300 and that can be detachably coupled via a female luer 356 to the male luer 334 of separation tubing 330.

It is also to be noted that FIGS. 3E-3F show an example where the sliding ring 350 is disposed in a first arrangement with the cutting element 352 being disposed on a side closer to the valve 306 than the viewing scope 348, whereas FIGS. 3G-3H show an example where the sliding ring 350 is disposed in a second arrangement with the cutting element 352 being disposed on a side further from the valve 306 than the viewing scope 348.

It is further to be noted that the sliding ring 350 may be formed from, or an assembly of, one or more parts or materials, and may adopt a ring shape or any other shape. The function of the sliding ring 350 is to appropriately position the cutting element 352, preferably in combination with a viewing scope 348 or the like, to cut the tubing 330 and achieve WBC isolation such as is described herein. As noted, the sliding ring 350 may be removable, may be attached to the tubing 330, or may be constrained in movement with respect to the tubing. In various non-limiting aspects, the sliding ring 350 is formed from a coated or non-coated polymer (e.g., HDPE, ABS, PVC, PEEK, PTFE, POM, etc.), metal, alloy, and etcetera. The sliding ring 350 need not fully circumscribe the tubing 300 and may only partially circumscribe the tubing. Further, the sliding ring 350 need not be continuous and may comprise, in a basic form, a movable guide member to provide accurate localization of the cutting element 352. In at least some aspects, the sliding ring 350 comprises a flat surface, such as is represented at the bottom of the sliding ring depicted in FIG. 4A, to permit the sliding ring to serve as a support member should the sliding ring and attached components (e.g., tubing 330) need to be rested on a flat surface.

According to one embodiment of a process in accord with aspects of the present concepts, a blood sample is added to a centrifuge tube 300, a suitable red blood cell lysing buffer is added to the blood sample, the centrifuge tube 300 is sealed tightly with a cap 302, and the centrifuge tube contents are gently mixed. Once most of the red blood cells have lysed, the sample is centrifuged for a predetermined amount of time at a predetermined rate, for example, for five minutes at 2000 rpm. The centrifugation causes the white blood cells and the RBCs that have not lysed to sediment into a cellular pellet. Most of the supernatant plasma-buffer is then aspirated and the red blood cells and white blood cells within the pellet can then be dispersed in the remaining plasma-buffer.

Figure 5A:
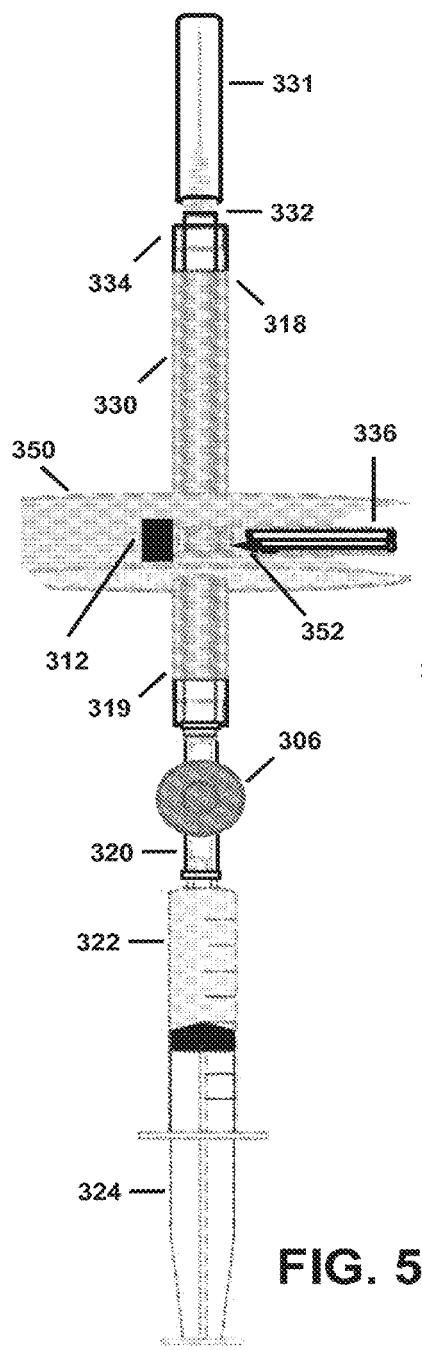
FIG. 5A is a view of the setup of one syringe, a tubing unit with a valve and a sliding ring with the blade positioned proximal to the valve, and a capped needle according to the embodiment shown in FIGS. 3A-3H.
Figure 5B:
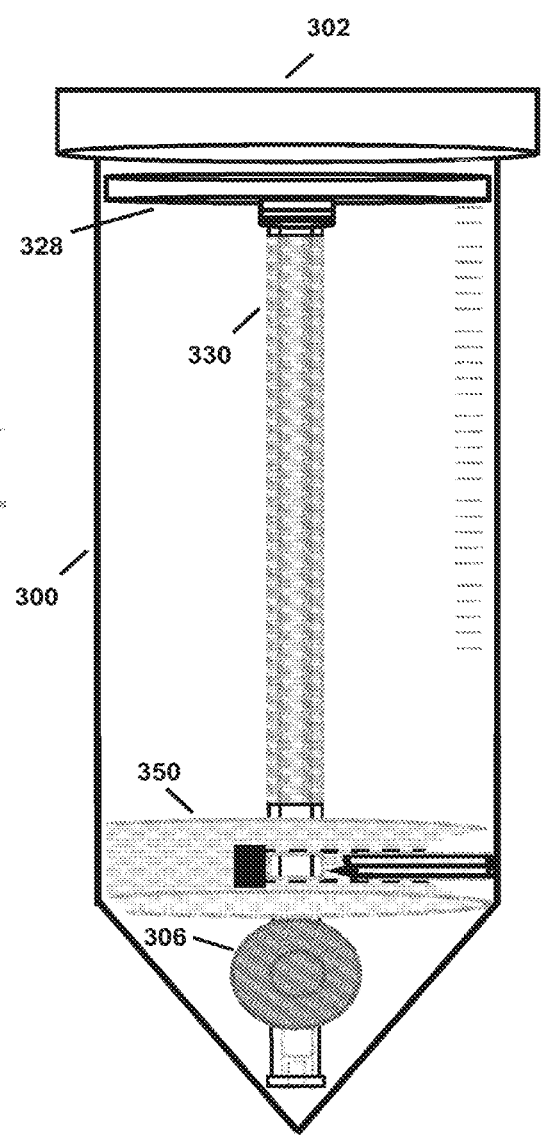
FIG. 5B is a view of a valve, a tubing unit, and a sliding ring whose blade is positioned proximal to the valve, with the tubing being distally capped and the whole setup being inside the centrifuge tube of FIG. 3A.

The tubing arrangement shown in FIG. 5A has a removably attached syringe 322 attached, at a proximal end, to a female luer 320 of valve 306 and a needle 332 with a cap 331 attached at its distal end 318. The sliding ring 350 in this tubing arrangement has its cutting element 352 disposed proximal to valve 306 (see also FIGS. 3E-3H). The valve 306 in this arrangement is first switched to the second position 310, as shown in FIG. 3D. The cap 331 is then removed and the contents of the centrifuge tube 300 including the red blood cell-white blood cell and plasma-buffer sample are aspirated into the tubing 330. The valve 306 is then switched to the first "closed" position 308, the needle 332 is capped, detached, and discarded, and cap 328 is detachably attached through its female luer 356 to the male luer 334 present at the distal end of tubing 330. The syringe 322 is then removed and the capped tubing setup and the sliding ring 350 coupled thereto are then placed inside the centrifuge tube 300, such as is shown by way of example in FIG. 5B. The cap 328 and the sliding ring 350 ensure that the tubing 330 is held within the center of the centrifuge tube 300. The centrifuge tube is centrifuged for a predetermined amount of time at a predetermined rate, for example for five minutes at 2000 rpm. The tubing 330 with the sliding ring 350 coupled thereto are then taken out of the centrifuge tube 300 and the setup, shown in FIG. 5C, is then advantageously placed on a flat surface for further processing.

Figure 5F:
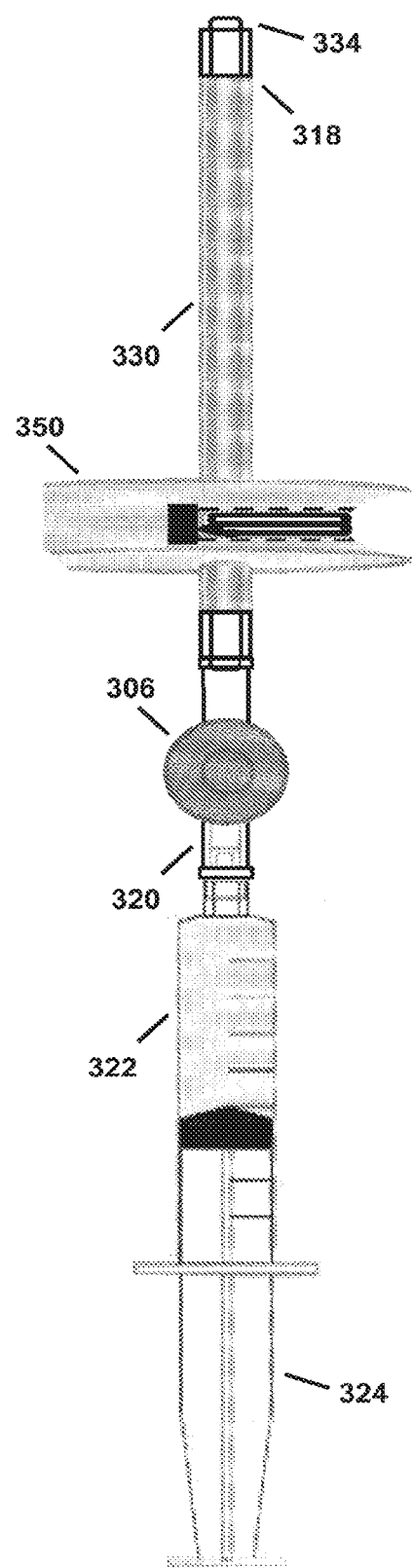
FIG. 5F is another view of a syringe connected to the valve-tubing unit with the sliding ring of FIG. 5E.
Figure 7:
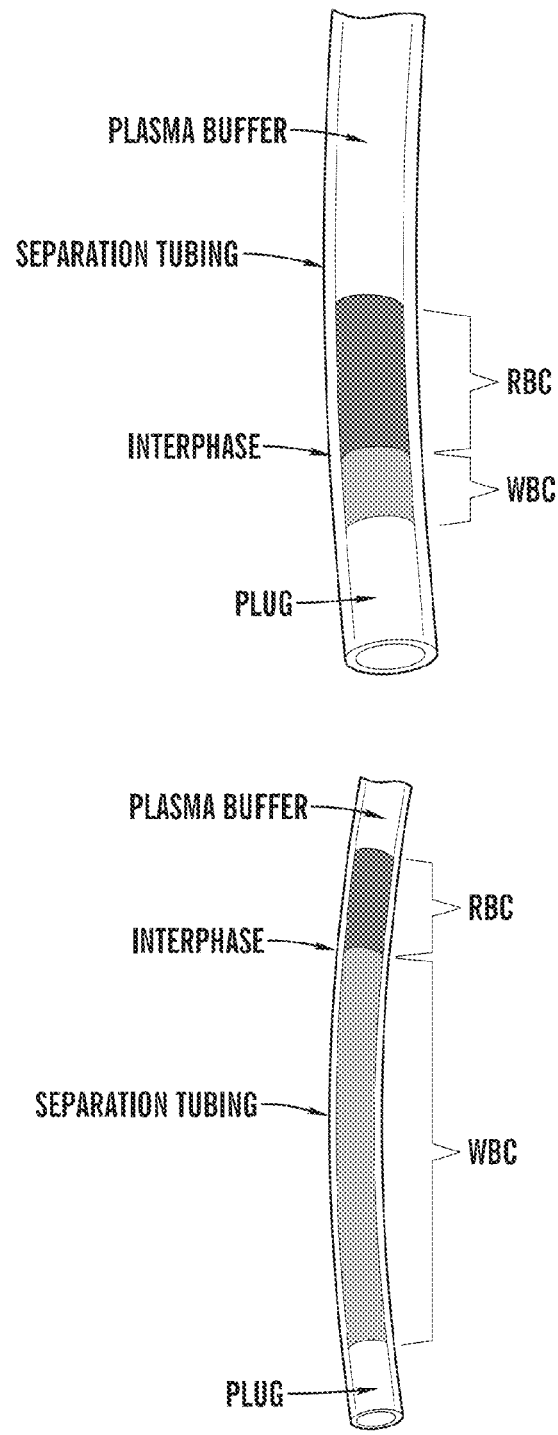
FIG. 7 shows the distinct separation of WBCs from RBCs in human blood samples that had been pretreated with RBC lysis buffer prior to their centrifugation (2000 rpm, 10 min) within Separation Tubes. Each of the Separation Tubes contains 3 distinct regions: plasma-buffer, RBC, and WBC.

Once the tubing 330 has been removed from the centrifuge tube 300 and situated for further processing, a user can then visually discern the relative locations of the plasma buffer, RBC, WBC and interphase therebetween (see, e.g., FIG. 7). In FIG. 5C, the location of the interphase is shown by the dashed line 354. The user can then slide the sliding ring 350 towards the location of the interphase 354 and, looking through the viewing eyepiece 344, which can comprise a viewing scope, can determine more precisely the location of the interphase 354 between the white blood cell and red blood cell layer, as shown in the sequence of FIGS. 5C-5D. In addition to the viewing eyepiece 344, or as an alternative thereto, a viewing window 351 is optionally provided in the sliding ring 350 to permit direct viewing of the tubing 330 in relation to the area traversed by the cutting element 352. In at least one aspect, a magnification device or lens is disposed in the viewing window to both seal the viewing window 351 to provide a fluid-tight seal as well as to facilitate resolution of the interphase. Once the sliding ring 350 is properly positioned at the interphase (FIG. 5D), a user can actuate the sliding board 338 to thereby cause the cutting element 352 to traverse and slice the tubing 330 at the interphase (FIG. 5E). This leads to the tubing unit 330 to have two parts: one part that is proximal to valve 306 and that includes the white blood cells and the other part that includes the red blood cells. The red blood cells layer is blocked behind the wall of the viewing unit 348, such as is shown in FIG. 4B. The opening 342 of the air tunnel 346 is positioned within the tubing 330 facing the white blood cells inside the tubing 330, as shown in FIG. 4B. A clean syringe 322 is then removably coupled to a female luer 320 at a proximal end of valve 306, as shown in FIG. 5F. The valve 306 is then switched to the second position 310 as shown in FIG. 3D, and the white blood cells can then be aspirated from the tubing 330 via the syringe 322. Air flows through the air tunnel 346 during the aspiration to vent the tube 330 and facilitate aspiration of the white blood cells. The white blood cells can then be dispensed from the syringe 322 into a container.

Embodiments of the present disclosure also provide for an automated cutting of the tubing 330, thereby allowing for a potentially higher yield and accuracy. The sliding ring 350 can include, or can be operated in conjunction with, a transmitter and a camera. The sliding ring 350 borne transmitter and camera, or external transmitter and camera, can be configured to transmit an image of the tubing contents to a processor, which could be a computer-based processing device or a user. The processor receives the image of the tubing contents and uses techniques known in the art, such as enlarging the image and/or utilizing edge and/or color detection techniques, to determine precisely the location of the interphase 354 between the red blood cell layer and the white blood cell layer. The processor (e.g., a computer) then transmits a signal to the sliding ring which causes the sliding ring to move along the tubing 330 toward the location of the interphase 354, such as is shown in the sequence of FIG. 5C-5D, such that the sharp end of the cutting element 352 is aimed precisely at the interphase location. The processor can then verify that the sliding board 338 is in fact positioned precisely at the interphase location and transmit a signal to the sliding ring 350 to cut the tubing 330. The user can then take a syringe and withdraw the contents of the tubing including the white cells and use such white cells in a variety of downstream applications. Alternatively, withdrawing of the white blood cells from the tubing can also be controlled by a processor.

According to another embodiment shown in FIG. 6, a blood sample can be added to a centrifuge tube 300. The cap 302 can then be removably attached to the centrifuge tube 300 and the sample can be centrifuged for a predetermined amount of time at a predetermined rate, for example for ten minutes at 2000 rpm. Most of the plasma layer above the buffy coat layer is then aspirated. The buffy coat layer is then carefully removed along with some of the red blood cells present below the buffy coat layer and transferred to a clean tube.

Figure 6A:
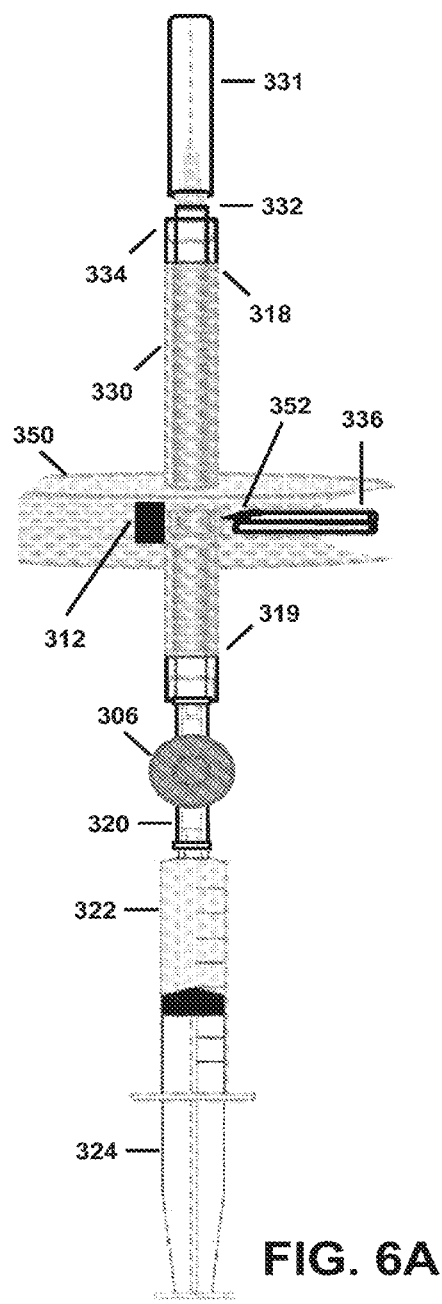
FIG. 6A is a view of the setup of one syringe, a tubing unit with a valve and a sliding ring with the blade positioned distal to the valve, and a capped needle according to the embodiment shown in FIGS. 3A-3H.
Figure 6B:
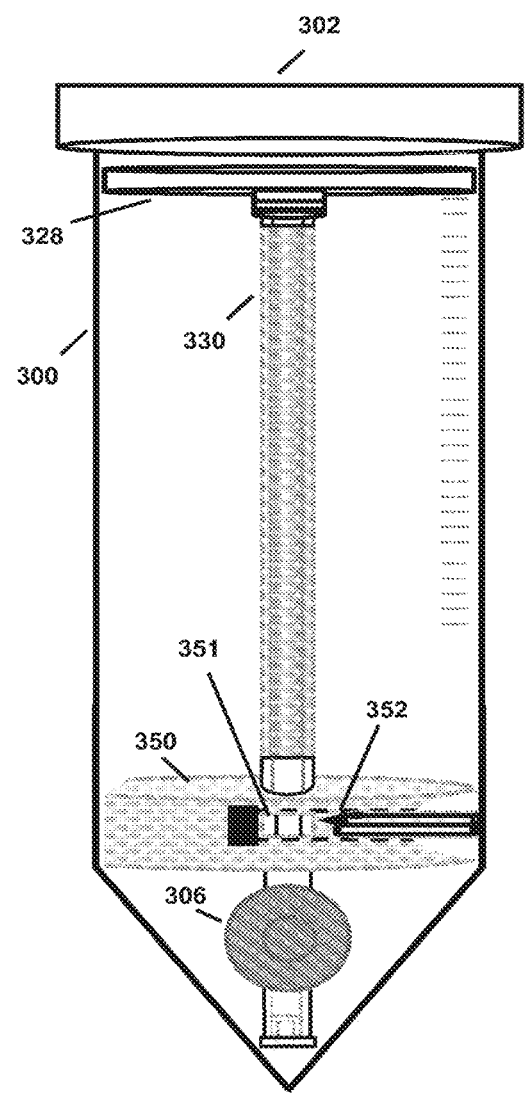
FIG. 6B is a view of a valve, a tubing unit, and a sliding ring whose blade is positioned distal to the valve, with the tubing being distally capped and the whole setup being inside the centrifuge tube of FIGS. 3A-3H.

The tubing arrangement shown in FIG. 6A has a removably attached syringe 322 attached to a female luer 320 at a proximal end and a needle 332 with a cap 331 is attached to a male luer 334 at its distal end 318. The sliding ring 350 in this tubing arrangement has its cutting element 352 distal to valve 306, such as is shown in FIGS. 3G-3H. The valve 306 in this arrangement is first switched to the second position 310 as shown in FIG. 3D. The needle cap 331 is then removed and the isolated buffy coat is aspirated into the tubing 330. The valve 306 is then switched to the first "closed" position 308, as shown in FIG. 3D, the needle 332 is capped, detached, and discarded, and cap 328 is detachably attached through its female luer 356 to the male luer 334 present at the distal end of tubing 330. The syringe 322 is then removed and the capped tubing setup and the sliding ring 350 coupled thereto are then placed inside the centrifuge tube 300 as shown in FIG. 6B. The substantial equality of the outer diameter of the cap 328 and the sliding ring 350 and the inner diameter of the centrifuge tube 300 ensure that the tubing 330 is securely held within the center of the centrifuge tube 300. The centrifuge tube is centrifuged for a predetermined amount of time at a predetermined rate, for example for five minutes at 2000 rpm. The tubing 330 with the sliding ring 350 coupled thereto are then taken out of the centrifuge tube 300 and the setup, shown in FIG. 6C, is positioned for further processing, such as by being placed on a flat surface.

Figure 6F:
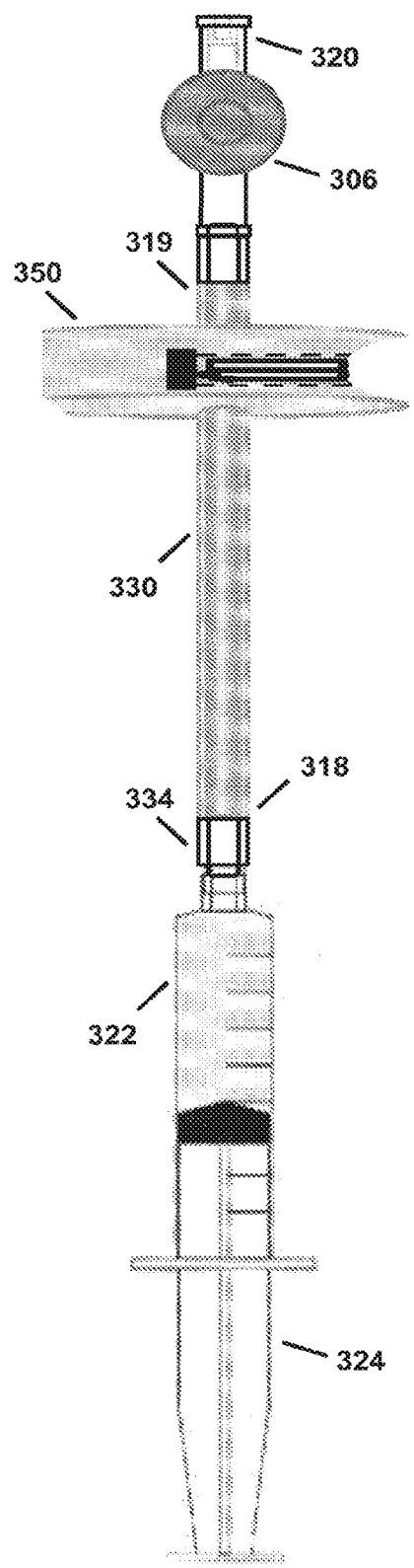
FIG. 6F is another view of a syringe connected to the distal end of the tubing unit with the sliding ring of FIG. 6E.

As described above, a user is then able to visually discern the relative locations of the plasma buffer, RBC, WBC and interphase therebetween (see, e.g., FIG. 7), look through the viewing eyepiece 344, which can be a viewing scope, and/or through an viewing window 351 comprising a lens or the like, to determine the location of the interphase 354 between the white blood cell and red blood cell layer, as shown in the sequence of FIGS. 6C-6D. In FIG. 6C, the location of the interphase is shown by the dashed line 354. The user can then slide the sliding ring 350 towards the location of the interphase and, looking through the viewing eyepiece 344, which can comprise a viewing scope, can determine more precisely the location of the interphase 354 between the white blood cell and red blood cell layer, as shown in the sequence of FIGS. 6C-6D. In addition to the viewing eyepiece 344, or as an alternative thereto, a viewing window 351 is optionally provided in the sliding ring 350 to permit direct viewing of the tubing 330 in relation to the area traversed by the cutting element. Once the sliding ring 350 is at the interphase (FIG. 6D), a user can actuate the sliding board 338 to cause the cutting element 352 to traverse and slice the tubing 330 at the interphase, as shown in FIG. 6E. This leads to the tubing unit 330 to have two parts: one part that is proximal to valve 306 and that includes the red blood cells and the other part that includes the white blood cells. The red blood cells layer is blocked behind the wall of the viewing unit 348, as shown in FIG. 4B. The opening of the air tunnel 342 is positioned within the tubing 330 facing the white blood cells inside the tubing 330, as shown in FIG. 4B. A clean syringe 322 is then removably coupled to the distal end 318 of tubing 330, as shown in FIG. 6F. The valve 306 is then switched to the second position 310, as shown in FIG. 3D, and the white blood cells can then be aspirated from the tubing 330 via the syringe 322. Air flows through the air tunnel 346 during the aspiration to vent the tube 330. The white blood cells can then be dispensed from the syringe 322 into a container.

Examples

Human blood was obtained from healthy blood donors at the Dana Farber Cancer Institute under an institutional review board-approved protocol with informed consent. A small volume (4 mL) of each blood sample was added to a centrifuge tube and an equal volume of red blood cell lysis buffer was then added and the components mixed gently. Once most of the red blood cells had lysed (within a few minutes), the samples were centrifuged at 2000 rpm for 10 min. After the centrifugation, most of the supernatant plasma-buffer was aspirated and the RBC/WBCs within the pellet washed once with PBS. The red blood cell and white blood cells within the washed pellets were then dispersed in ~100 □L of the plasma buffer and aspirated into a tubing (internal i.d. 1.22 mm, 15 cm long). The tubings were each plugged with a paper clip and the plugged tubings placed inside a 15 mL centrifuge tube, which was then centrifuged at 2000 rpm for 5 min. The tubings were removed and photographed. FIG. 7 shows two such RBC-WBC separations showing the clear interphase between the RBCs and the WBCs.

While particular embodiments and applications of the present invention have been illustrated and described, it is to be understood that the invention is not limited to the precise constructions and arrangements disclosed herein and that various modifications, changes, and variations can be apparent to those having ordinary skill in the art from the foregoing descriptions without departing from the spirit and scope of the invention as defined in the appended claims.

What is claimed is:

1. A method for isolating white blood cells from blood, comprising:
   a) adding a blood sample to a separation tube having a distal end, a proximal end, and a valve located at said proximal end of the separation tube, said valve being configured to transition between at least first, second, and third positions;
   b) removably attaching a cap to the distal end and centrifuging the separation tube including the valve with the valve in the first position;
   c) removing the cap at the distal end of the separation tube and removably attaching a first syringe to the valve at the proximal end;
   d) switching the valve to the second position;
   e) withdrawing through the valve, via the first syringe, a red blood cell sediment;
   f) switching the valve to the first position and removing the first syringe;
   g) adding a small volume of buffer to the separation tube;
   h) removably attaching a cap to the distal end and centrifuging the separation tube including the valve;
   i) removing the cap at the distal end of the separation tube and removably attaching a second syringe to the valve at the proximal end;
   j) switching the valve to the second position;
   k) withdrawing the remaining red blood cell sediment through the valve via the second syringe; and
   l) switching the valve to the first position and removing the second syringe.

2. The method of claim 1, further comprising:
   m) removably attaching a third syringe to the valve at the proximal end; and
   n) switching the valve to the third position and withdrawing white blood cells through the valve via the third syringe.

3. The method of claim 2, further comprising:
   o) switching the valve to the first position and removing the third syringe; and
   p) dispensing the white blood cells from the third syringe into a container.

4. The method of claim 1, wherein withdrawal of the red blood sediment via the first syringe is performed until a red blood cell buffy coat is within a neck of the separation tube.

5. The method of claim 1, wherein the withdrawing of the remaining red blood cell sediment is performed by rotating a plunger of the second syringe.

6. The method of claim 1, wherein flow out of the proximal end is blocked when the valve is in the first position.

7. The method of claim 1, wherein the method is configured to be completed in 30 minutes.

8. A method for isolating white blood cells from blood, comprising:
   a) adding a blood sample to a separation tube having a distal end, a proximal end, and a valve located at said proximal end, said valve being configured to switch between at least first and second positions;
   b) adding a red blood cell lysing buffer to said blood sample and mixing said buffer with said blood sample;
   c) removably attaching a cap to the distal end and centrifuging said separation tube including the valve with the valve in the first position;
   d) removing the cap at the distal end of the separation tube and removably attaching a first syringe to the valve at said proximal end;
   e) switching said valve to said second position; and
   f) withdrawing a white blood cell sediment through the valve via said first syringe.

9. The method of claim 8, further comprising:
   g) dispensing the white blood cell sediment from the first syringe into a container.

10. The method of claim 8, wherein the withdrawing the white blood cell sediment is performed by rotating a plunger of the first syringe.

11. The method of claim 8, wherein flow out of the proximal end is blocked when the valve is in the first position.

12. The method of claim 8, wherein the method is configured to be completed in 15 minutes.

13. A method of isolating white blood cells from blood, comprising:
   a) adding a blood sample to a centrifuge tube and centrifuging the centrifuge tube;
   b) aspirating most of a plasma layer; and
   c) removing a buffy coat containing a red blood cell and white blood cell mixture;
   d) adding the buffy coat to a separation tube having a distal end, a proximal end, and a valve coupled to said proximal end, said valve being configured to transition between a first position, a second position, and a third position, each of the second and third positions defining separate fluid passages;
   e) filling the separation tube with a suitable buffer;
   f) removably attaching the cap to the distal end and centrifuging the separation tube including the valve with the valve in the first position;
   g) removing the cap at the distal end of the separation tube following the act of centrifuging the separation tube and removably attaching a first syringe to the valve at the proximal end;
   h) switching the valve to the second position;
   i) withdrawing a sedimented red blood cell layer through the valve, via the first syringe; and
   j) switching the valve to the first position and removing the first syringe.

14. The method of claim 13, further comprising:
   k) removably attaching a second syringe to the valve at the proximal end and switching the valve to the third position;
   l) withdrawing a white blood cell layer through the valve, via the second syringe; and m) rotating the valve to the first position, removing the second syringe, and dispensing the white blood cell layer into a container.

* * * * *